(12) United States Patent
Lum

(10) Patent No.: US 8,882,794 B2
(45) Date of Patent: Nov. 11, 2014

(54) LANCET DEVICE WITH LANCE RETRACTION

(71) Applicant: Wah Leong Lum, Singapore (SG)

(72) Inventor: Wah Leong Lum, Singapore (SG)

(*) Notice: Subject to any disclaimer, the term of this patent is extended or adjusted under 35 U.S.C. 154(b) by 0 days.

(21) Appl. No.: 13/654,517

(22) Filed: Oct. 18, 2012

(65) Prior Publication Data

US 2013/0041393 A1 Feb. 14, 2013

Related U.S. Application Data

(62) Division of application No. 12/511,475, filed on Jul. 29, 2009, now Pat. No. 8,317,812.

(51) Int. Cl.
*A61B 17/14* (2006.01)
*A61B 5/15* (2006.01)
*A61B 5/151* (2006.01)

(52) U.S. Cl.
CPC ............ *A61B 5/1411* (2013.01); *A61B 5/15128* (2013.01); *A61B 5/1513* (2013.01); *A61B 5/150022* (2013.01); *A61B 5/150893* (2013.01); *A61B 5/150541* (2013.01); *A61B 5/15117* (2013.01); *A61B 5/15144* (2013.01); *A61B 5/150503* (2013.01); *A61B 5/150412* (2013.01); *A61B 5/15111* (2013.01)
USPC .......................................... 606/181; 600/573

(58) Field of Classification Search
USPC ............................ 606/181, 182; 600/573, 583
See application file for complete search history.

(56) References Cited

U.S. PATENT DOCUMENTS

| | | |
|---|---|---|
| 4,203,446 A | 5/1980 | Hofert et al. |
| 4,375,815 A | 3/1983 | Burns |
| 4,445,510 A | 5/1984 | Rigby |
| 4,469,110 A | 9/1984 | Siama |
| 4,628,929 A | 12/1986 | Intengan et al. |
| 4,735,203 A | 4/1988 | Ryder et al. |
| 5,196,025 A | 3/1993 | Ranalletta et al. |
| 5,212,879 A | 5/1993 | Biro et al. |
| 5,402,798 A | 4/1995 | Swierczek et al. |
| 5,643,306 A | 7/1997 | Schraga |

(Continued)

FOREIGN PATENT DOCUMENTS

| | | |
|---|---|---|
| WO | WO 2005/110228 A1 | 11/2005 |
| WO | WO/2006/110742 | 10/2006 |

OTHER PUBLICATIONS

Supplementary European Search Report for EP 10 80 4798, European Patent Office, Oct. 24, 2012.

*Primary Examiner* — Victor Nguyen
(74) *Attorney, Agent, or Firm* — Porter, Wright, Morris & Arthur, LLP

(57) ABSTRACT

A lancet device includes a hollow housing defining a cavity and having a proximal end and a distal end and a slider slidable at least partially within the cavity along a longitudinal axis from an outward position to a pushed position. The slider extends outside of the cavity beyond the proximal end when it is in the outward position. A needle holder holding a needle is rotatable about and translatable along the longitudinal axis when moved from an initial position to an extended position. When the needle holder is in the initial position, the slider is in the outward position. When the needle holder is in the extended position, the lance extends beyond the proximal end. Sliding of the slider to the pushed position enables a first biasing member to urge the needle holder toward the extended position. A second biasing member can be present in the lancet device.

7 Claims, 32 Drawing Sheets

(56) References Cited

U.S. PATENT DOCUMENTS

| | | |
|---|---|---|
| 5,741,288 A | 4/1998 | Rife |
| 5,797,940 A | 8/1998 | Mawhirt et al. |
| 6,042,595 A | 3/2000 | Morita |
| 6,156,050 A | 12/2000 | Davis et al. |
| D455,830 S | 4/2002 | Hommann et al. |
| 6,432,120 B1 | 8/2002 | Teo |
| 6,464,649 B1 * | 10/2002 | Duchon et al. ............... 600/583 |
| 6,540,762 B1 | 4/2003 | Bertling |
| 6,540,763 B2 | 4/2003 | Teo et al. |
| D526,409 S | 8/2006 | Nielson et al. |
| 7,105,006 B2 | 9/2006 | Shraga |
| 7,311,718 B2 * | 12/2007 | Schraga ....................... 606/181 |
| 7,374,544 B2 | 5/2008 | Freeman et al. |
| 2009/0036915 A1 | 2/2009 | Karbowniczek et al. |

\* cited by examiner

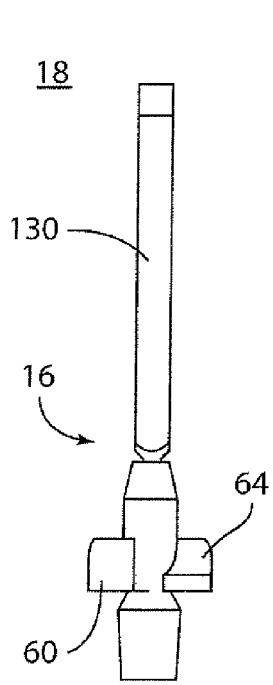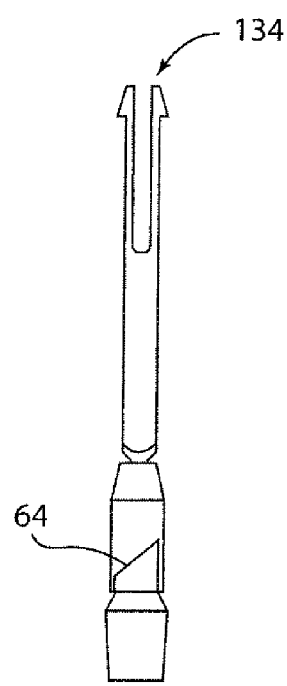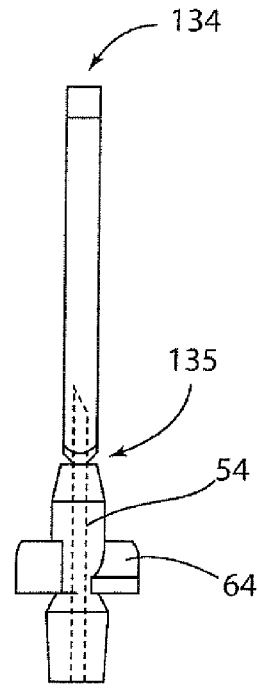
Fig. 14A　　　Fig. 14B　　　Fig. 14C
Fig. 14D
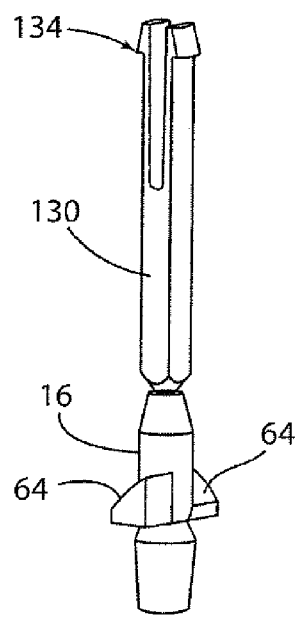
Fig. 14E

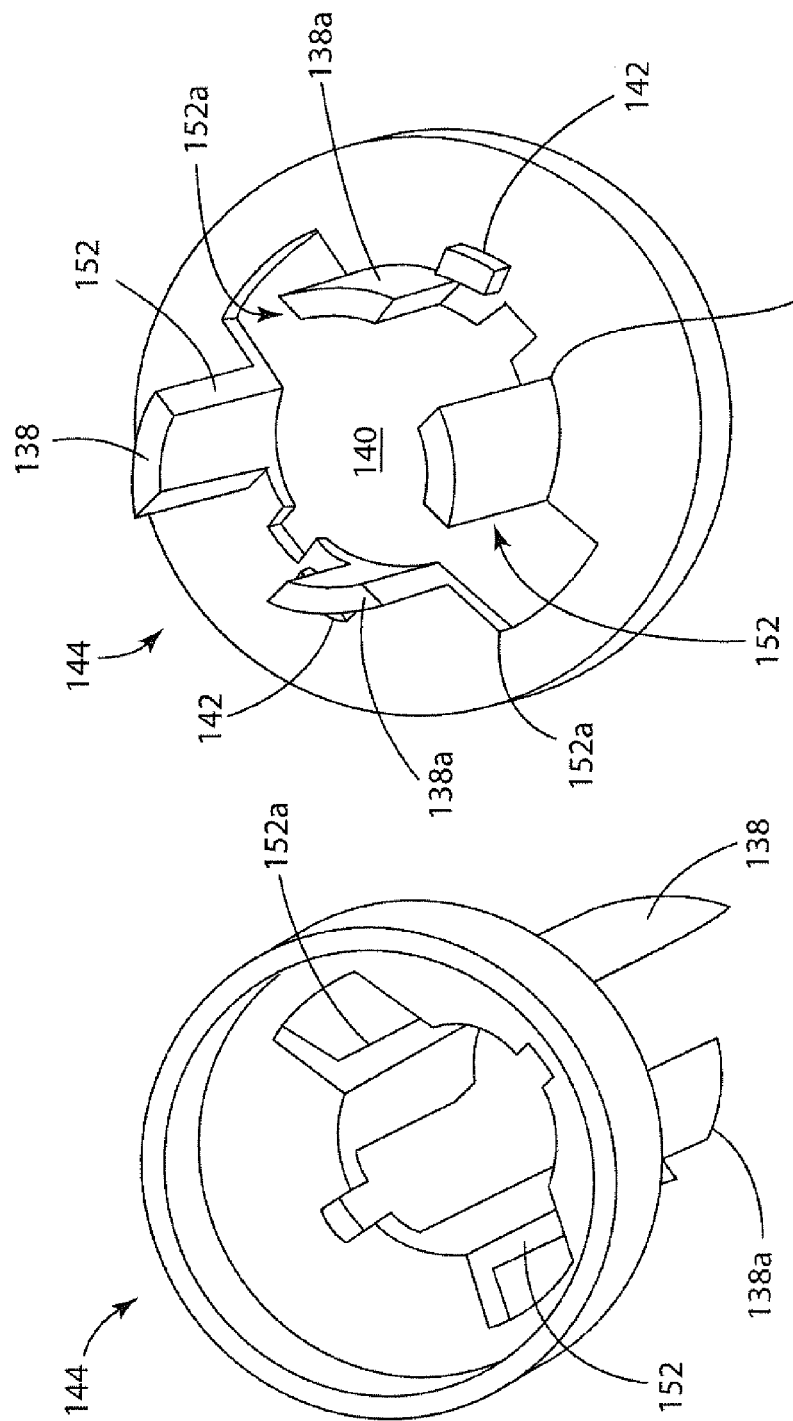

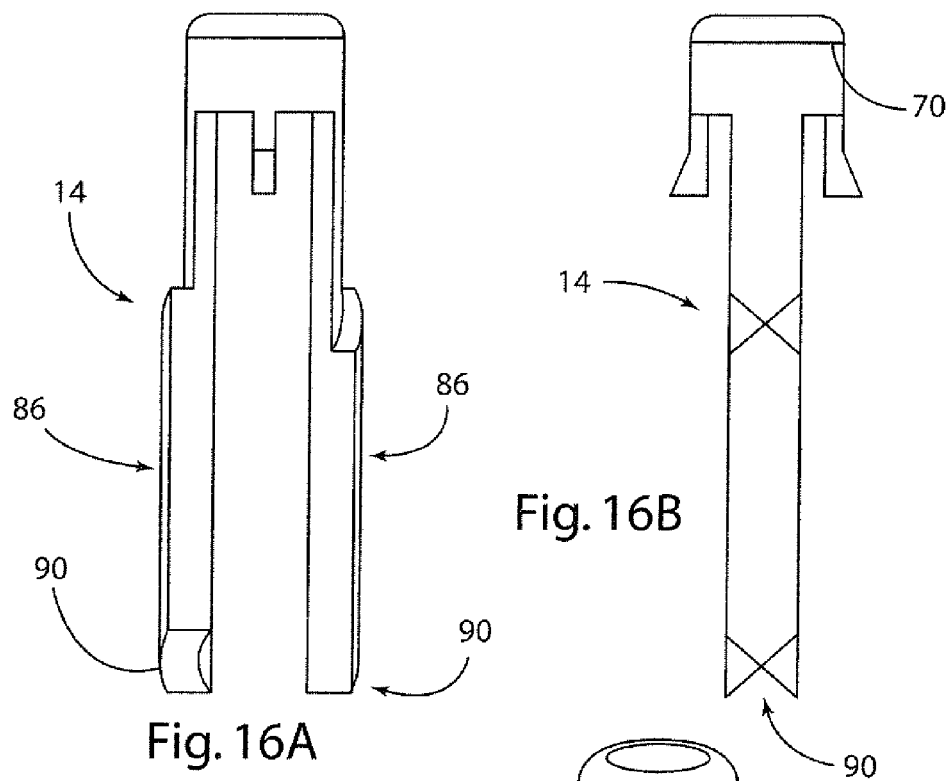
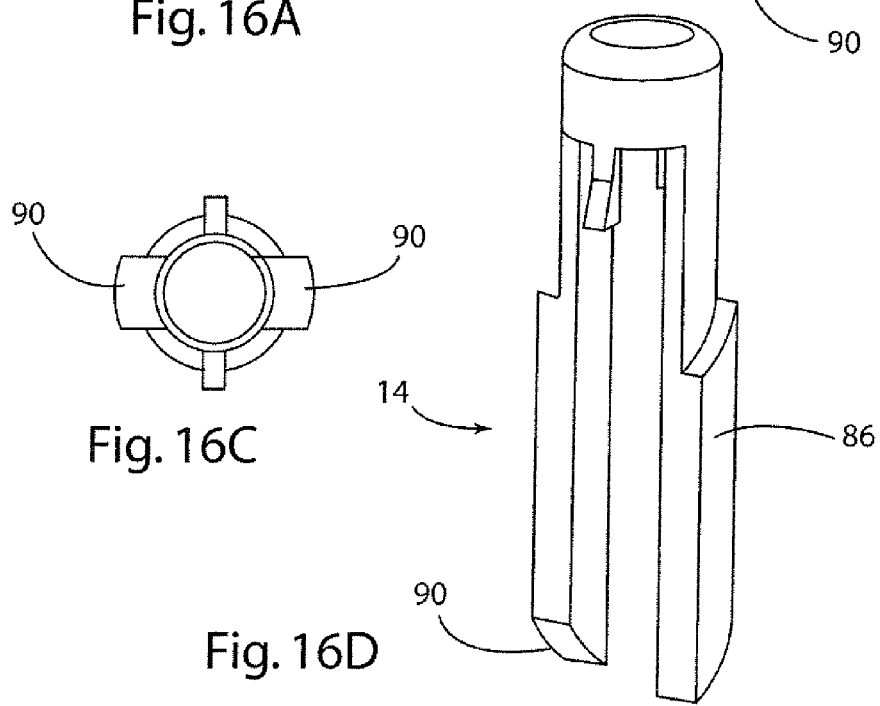
Fig. 16A  Fig. 16B  Fig. 16C  Fig. 16D

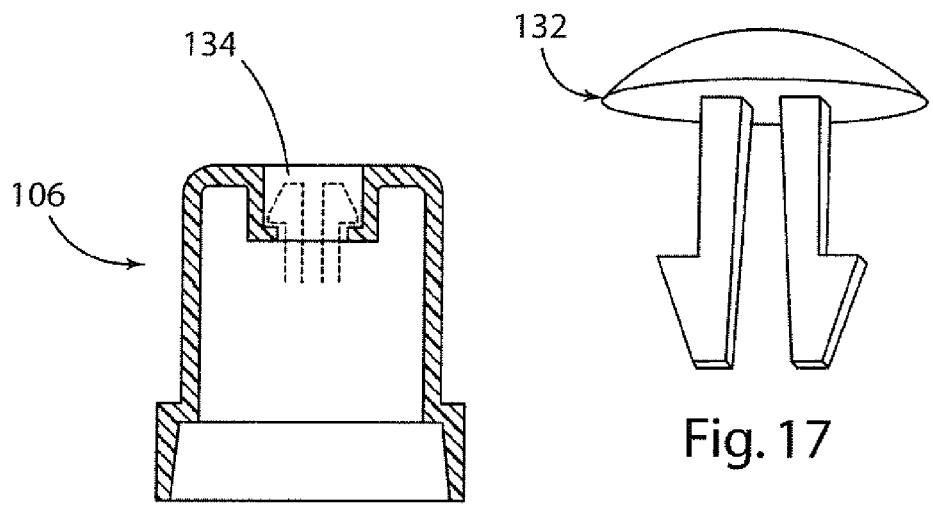
Fig. 17
Fig. 18A
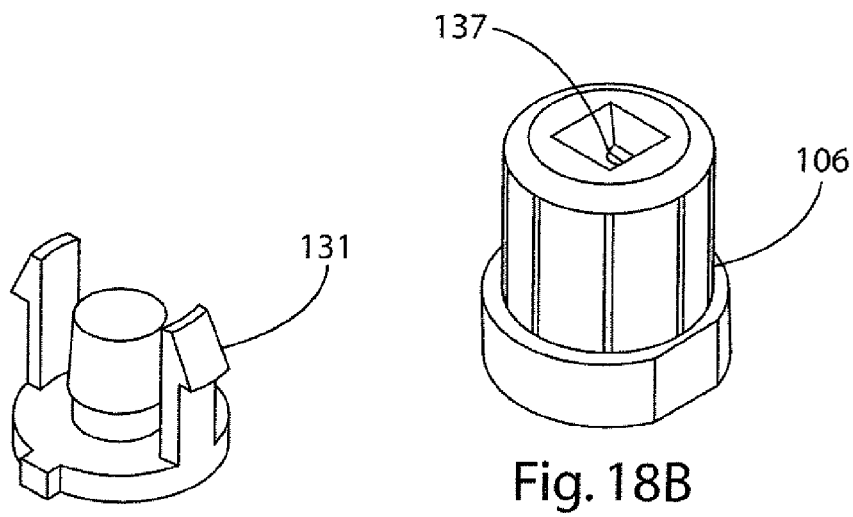
Fig. 19
Fig. 18B

LANCET DEVICE WITH LANCE RETRACTION

CROSS REFERENCE TO RELATED APPLICATIONS

This application is a divisional application of U.S. patent application Ser. No. 12/511,475 filed on Jul. 29, 2009, the disclosure of which is expressly incorporated herein in its entirety by reference.

FIELD OF THE INVENTION

The invention relates generally to lancet devices used in taking blood samples from patients, and more specifically to lancet devices activated by contact with the patient's skin or tissue.

BACKGROUND OF THE INVENTION

Lancet devices are commonly used both in medical facilities and by private individuals to obtain a blood sample from a patient by puncturing the skin of the patient. This is used when only a small amount of blood is required. Diseases, such as diabetes use blood testing at regular intervals to monitor blood sugar levels of the patient. Obtaining a sample of blood usually involves pricking a finger or other suitable body part with a needle. In view of blood-borne diseases, it is important that, after use of the lancet, other persons do not come into contact with the lancet. Thus, an important aspect of a lancet device involves preventing the needle from wounding another person after the skin of the patient has been punctured. The lancet should be shielded, after use of the device, to prevent accidental wounding of another person. Further, the lancet should be disposable to reduce the possibility of disease transmission due to the device being used on other persons. In this respect, the lancet should preferably be a single use device with features to prevent reuse.

U.S. Pat. No. 6,432,120 B1 to Teo discloses a contact activated lancet. 1 The device has a needle holder and a triggler (triggering device) enclosing a lancet structure. The triggler interacts with the needle holder via a triggering element to maintain the spring in a compressed state such that the lancet structure is in a stable standby position which is not easily triggered by accidental bumps on the assembly. The device is assembled with the spring in the compressed state. Lancets such as those disclosed in Teo are pre-armed prior to use on a patient. With pre-armed lancets there is a potential of triggering prior to application on a patient's skin rendering the device not usable.

WO 2005/110227 A1 to Karbowniczek et al discloses a contact activated lancet including a lancet structure with a puncturing element within a housing structure. The device includes a drive spring and a pivotal lever in interference engagement with the lancet structure. An actuator within the housing pivots the lever, to move the lancet structure toward the rearward end of the housing to at least partially compress the drive spring and thereby releasing the lever from interference engagement with the lancet structure allowing the lancet structure to propel forward. Karbowniczek et al discloses a complicated arrangement for retaining and releasing the lancet structure and is difficult to manufacture and assemble.

It would be desirable to provide a robust, disposable lancet device of simple construction which effectively reduces the likelihood of the lance triggering prior to application.

SUMMARY OF INVENTION

In accordance with a first aspect, a lancet device comprises a hollow housing defining a cavity and having a proximal end and a distal end. It also comprises a slider slidable at least partially within the cavity of the hollow housing along a longitudinal axis from an outward position to a pushed position. The slider extends outside of the cavity beyond the proximal end of the hollow housing when it is in the outward position. The lancet device also comprises a needle holder holding a lance. The needle holder is rotatable about and translatable along the longitudinal axis when moved from an initial position to an extended position. When the needle holder is in the initial position, the slider is in the outward position. When the needle holder is in the extended position, the lance extends outside of the cavity beyond the proximal end of the hollow housing. The sliding of the slider from the outward position to the pushed position urges the needle holder to the extended position. There is also a first biasing member positioned within the hollow housing at the distal end. The first biasing member exerts a biasing force against the needle holder toward the proximal end when the slider is moved to the pushed position. There is also a second biasing member in the lancet device.

From the foregoing disclosure and the following more detailed description of various preferred embodiments it will be apparent to those skilled in the art that the present invention provides a significant advance in the technology of lancet devices. Particularly significant in this regard is the potential the invention affords for providing a lancet device with improved reliability. Additional features 1 and advantages of various preferred embodiments will be better understood in view of the detailed description provided below.

BRIEF DESCRIPTION OF DRAWINGS

FIG. 10(a) shows the arrangement prior to activation of the slider by pressing the device against the patient's tissue, FIG. 10(b) shows the movement of the slider and needle holder towards the housing distal end relative to the short rail and against the biasing means, e.g. a spring, FIG. 10(c) shows alignment of the contact surface of the needle holder with the end wall of the short rail, and the start of the sliding of the arm of the lancet down this included composite surface, due to the combination of the inclined surface and the biasing means or spring, FIG. 10(d) shows the arm having slide off the inclined composite surface and moving down into the gap next to the short rail, FIG. 10(e) shows the lancet exiting the housing of the device to puncture the patient's skin or tissue, due to the movement imparted to it by the biasing means, and FIG. 10(f) shows the lancet being retracted into the device as the biasing means over comes its movement caused over extension, to leave the lancet within the housing.

FIG. 14 shows the needle holder at (a) front view, (b) right hand side view, (c) back view with hidden detail showing the lancet, (d) plan view, and (e) isometric view.

FIG. 15(a)-15(f) show the guide body in (a) front view, (b) vertical sectional view along line B-B, (c) bottom view, (d) isometric view, (e) bottom isometric view, and (f) top isometric view.

FIG. 16(a)-16(d) show the slider in: (a) a front view, (b) a side view, (c) bottom view, and (d) isometric view.

FIG. 17 shows the cap cover in bottom isometric view.

FIG. 18(a)-18(b) show the cap at (a) in vertical sectional view 1 and (b) isometric view.

FIG. 19 shows the base cap of the second embodiment in top isometric view.

Figure 1:
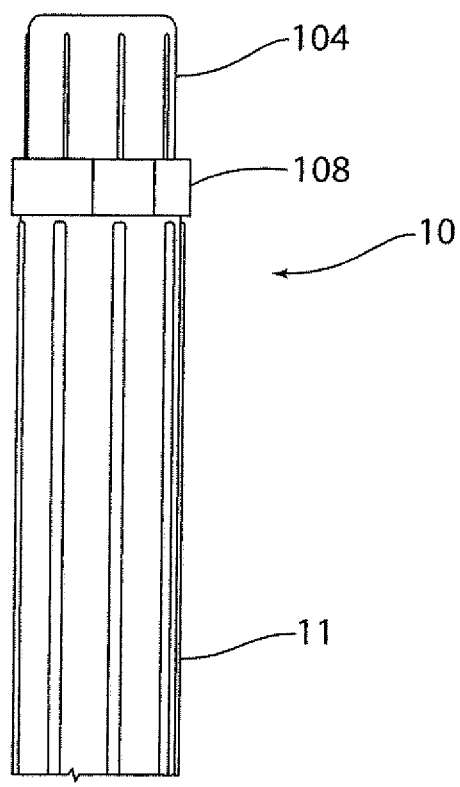
FIG. 1 is a side view of a lancet in accordance with an embodiment of the invention.

It should be understood that the appended drawings are not necessarily to scale, presenting a somewhat simplified representation of various preferred features illustrative of the basic principles of the invention. The specific design 1 features of the lancet as disclosed here, including, for example, the specific dimensions of the lancet, will be determined in part by the particular intended application and use environment. Certain features of the illustrated embodiments have been enlarged or distorted relative to others to help provide clear understanding. In particular, thin features may be thickened, for example, for clarity of illustration. All references to direction and position, unless otherwise indicated, refer to the orientation illustrated in the drawings.

DETAILED DESCRIPTION OF CERTAIN EMBODIMENTS

It will be apparent to those skilled in the art, that is, to those who have knowledge or experience in this area of technology, that many uses and design variations are possible for the lancet devices disclosed here. The following detailed discussion of various alternative and preferred features and embodiments will illustrate the general principles of the invention with reference to a lancet device suitable for use in blood sample testing. Other embodiments suitable for other applications will be apparent to those skilled in the art given the benefit of this disclosure.

Figure 2:
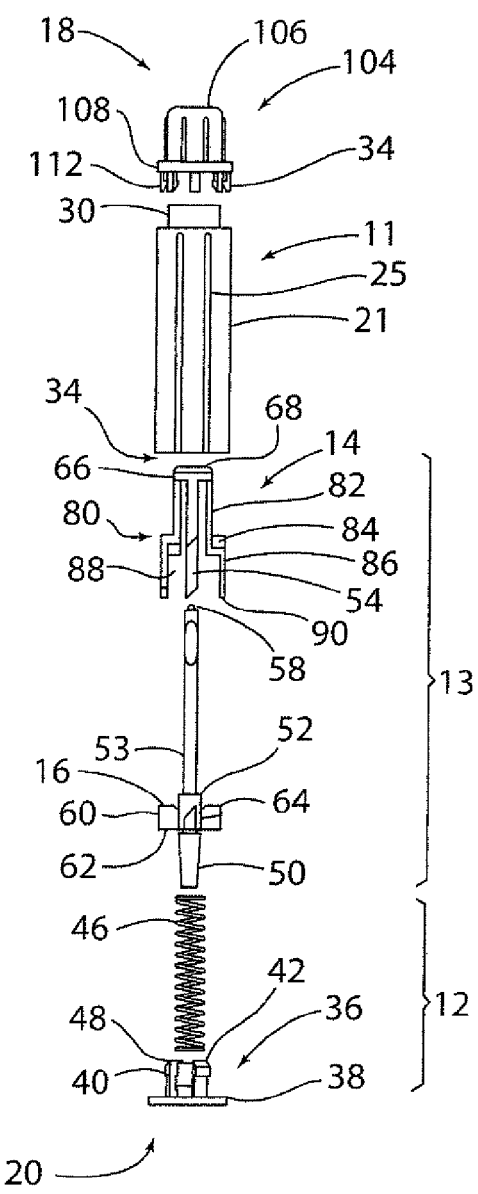
FIG. 2 is an exploded view of lancet of FIG. 1.
Figure 3:
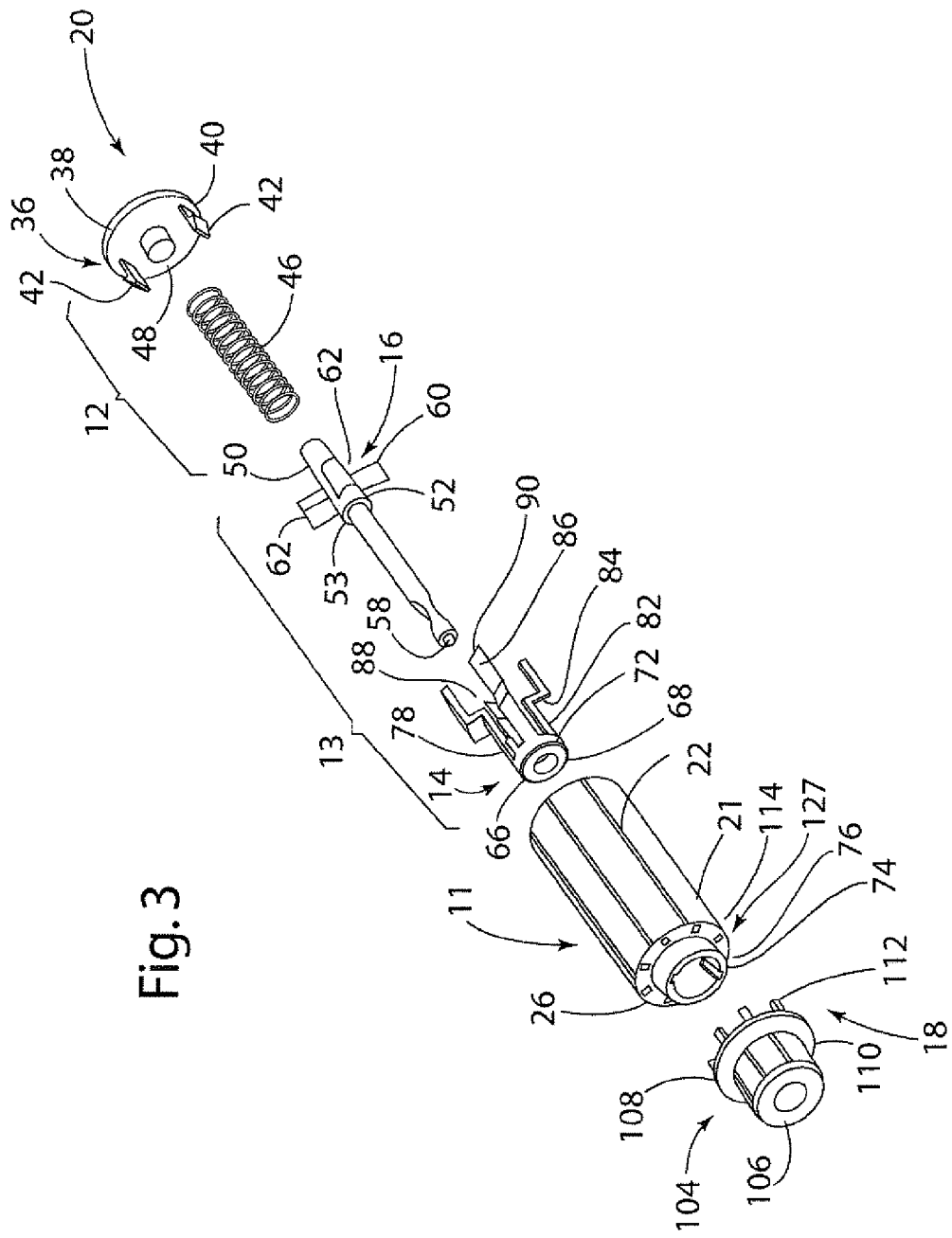
FIG. 3 is an exploded isometric view of lancet of FIG. 1.
Figure 4:
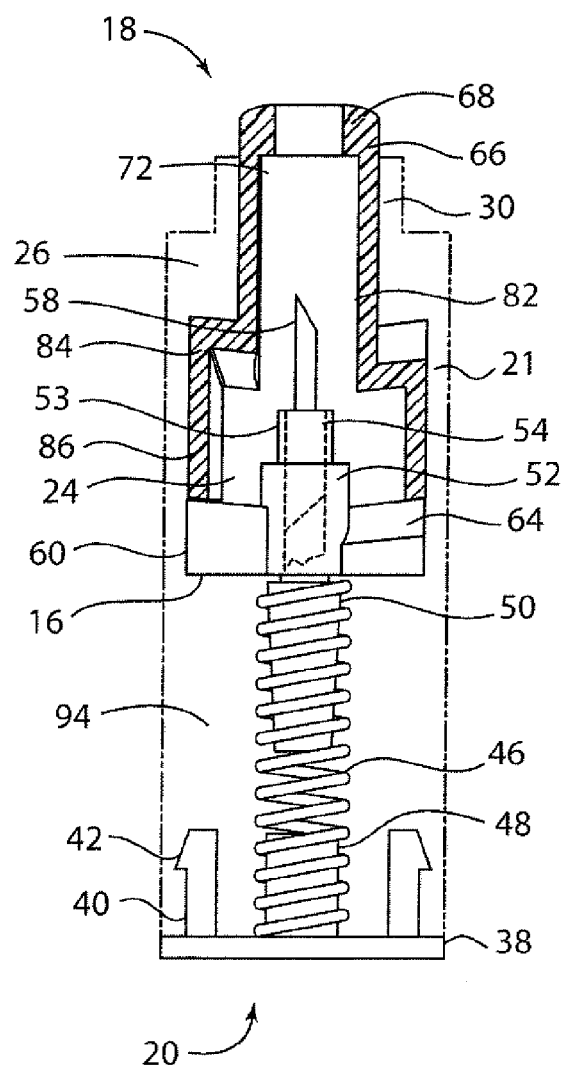
FIG. 4 is a cross-section side view of a pre-actuated lancet.
Figure 5:
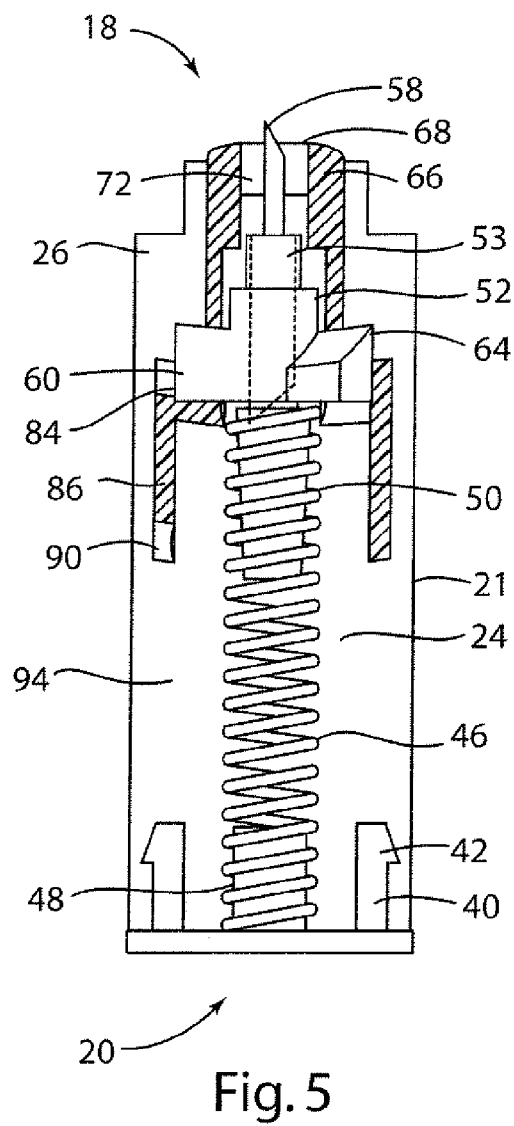
FIG. 5 is a cross-section side view of an actuated (first condition) lancet with the needle holder as a structure for holding the lancet in a puncture position.
Figure 6:
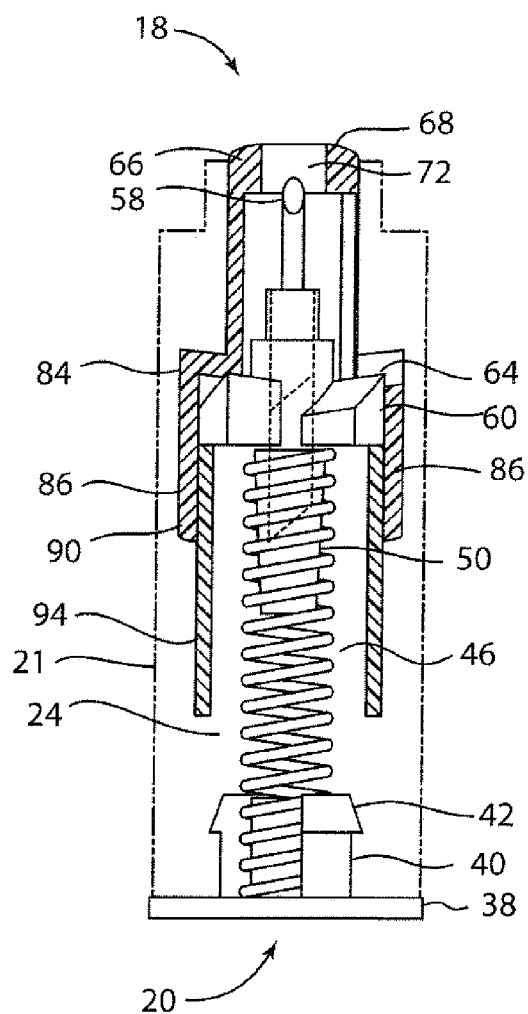
FIG. 6 is a cross-section side view of an actuated lancet with the needle holder retracted within the housing after executing a puncture.
Figure 7:
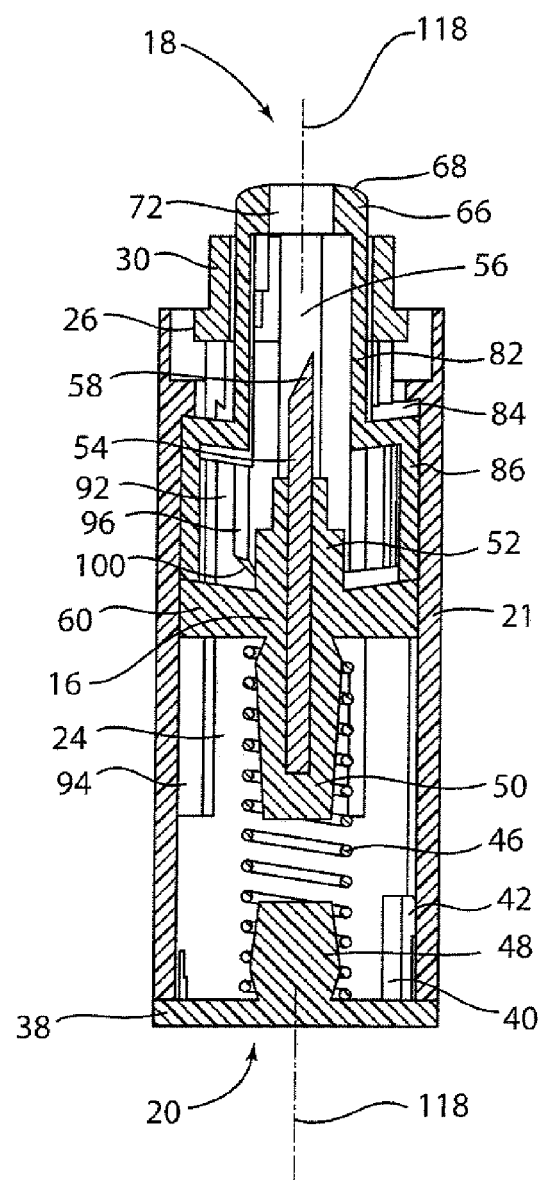
FIG. 7 is a schematic side view of a pre-actuated lancet.
Figure 8:
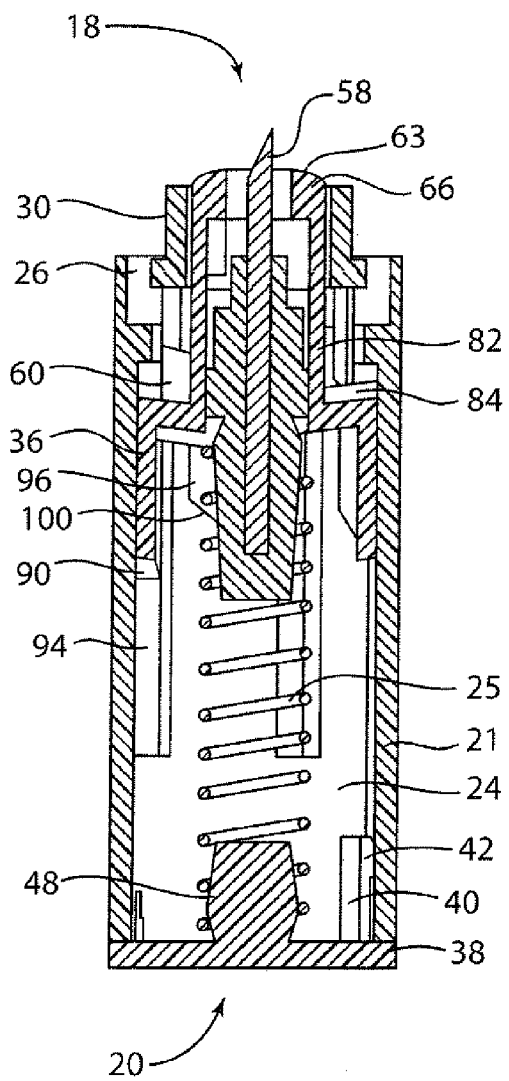
FIG. 8 is a schematic side view of an actuated lancet with the needle holder in a puncture position.
Figure 9:
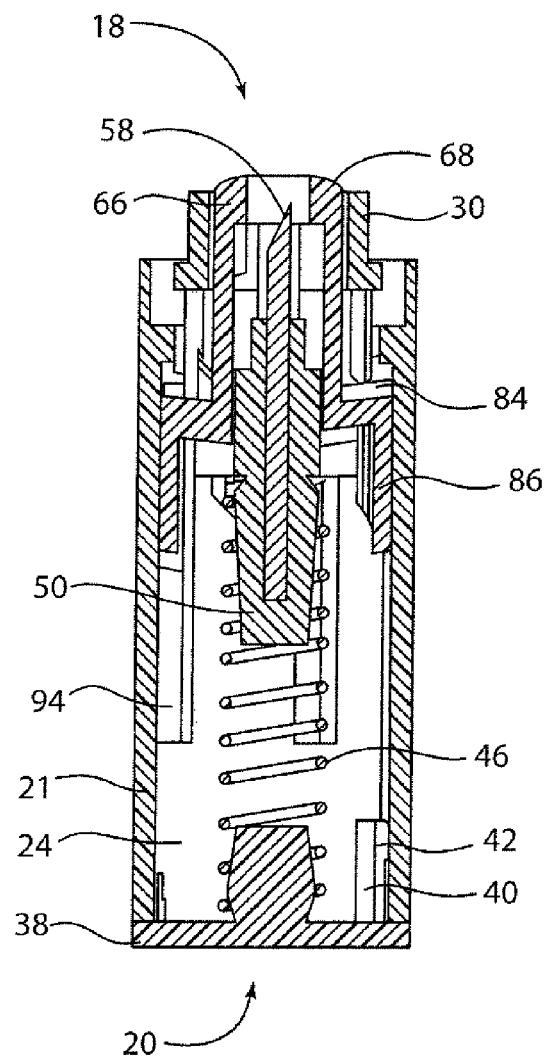
FIG. 9 is a schematic side view of an actuated lancet with the needle holder retracted within the housing after executing a puncture.

With reference to the above drawings, FIG. 1 shows a side view of a lancet device 10 with a hollow housing 11, a cover 104 and a ring 108. FIG. 2 shows an exploded isometric view of a first embodiment of lancet device 10. Lancet device 10 generally includes a hollow housing 11, a biasing assembly 12 and a lancet subassembly 13 movably associated with the hollow housing 11. The lancet subassembly 13 includes a slider 14 and a needle holder 16. The hollow housing 11 has a proximal end 18, which is the end placed on the skin or tissue 116 of a patient to be punctured, and a distal end 20, which is the end opposite to the proximal end 18. The proximal end 18 of the hollow housing has a proximal end opening 127.

Slider 14 is in part disposed within the hollow housing 11 and a patient contact portion or abutment surface extends partially from the hollow housing 11 at the proximal end 18 via the proximal end opening 127.

Lancet subassembly 13 is axially or longitudinally movable within the hollow housing 11. Needle holder 16 is operatively associated with slider 14. It is to be understood that such axial movement includes any movement of the slider 14 and the needle holder 16 relative to each other, including axial and/or rotational movement of either element or both elements with respect to the general length of hollow housing 11.

Hollow housing 11 may be formed integrally. Alternatively hollow housing 11 may be formed in separate parts, divided lengthwise or otherwise. Each part may be affixed to each other through an appropriate adhesive or through appropriate inter engaging structures which provide a mechanical attachment between the parts, such as frictional fit or snap fit construction.

The hollow housing 11 includes an elongated body 21, both having a common central longitudinal axis. It is to be understood that body 21 may 1 be formed in any suitable form. Preferably body 21 is cylindrical. The interior of body 21 is generally hollow. Body 21 has an interior wall 22 of an annular cross-section. Interior wall 22 defines a uniform cylindrical internal cavity 24 which extends from the proximal end 18 to the distal end 20. Slider 14 and needle holder 16 are contained within internal cavity 24. Body 21 may have plurality of external ribs 25 extending longitudinally from the distal end 20 to the proximal end 18 of hollow housing 11. Ribs 25 aid the patient in gripping lancet device 10. Other configurations can be used to provide a surface which improves the grip of lancet device 10. For example outer surface of body 22 may be configured to accommodate a patient's finger, such as finger grip indentations or may be textured or otherwise.

In the preferred embodiment housing 11 includes a rim 26 extending from body 21 and inward of the central longitudinal axis of body 21, outer edge of rim 26 being joined to body 21. Preferably rim 26 is perpendicular to body 21. Rim 26 partially seals internal cavity 24 at the proximal end 18 of hollow housing 11. The inner edge of rim 26 encircles an annular aperture 28. Aperture 28 communicates with internal cavity 24. Hollow housing 11 may include a collar 30 which projects from rim 26 parallel to the central longitudinal axis of body 21 stretching around the inner edge of rim 26 and thereby encircling a vestibule 32. One end of vestibule 32 is aperture 28. Vestibule 32 and aperture 28 have equivalent diameters. Opposite to aperture 28 is an opening 33 of vestibule 32. Vestibule 32 communicates with internal cavity 24 through aperture 28.

Rim 26 and collar 30 may be integrally formed with body 21. 1 Alternatively, rim 26 and collar 30 may be formed as a unitary component separate from and then affixed to body 21. In such a configuration rim 26 with collar 30 is affixed to proximal end 18 of body 21 through an appropriate adhesive or through an appropriate inter engaging structure, such as frictional fit, snap fit construction or threaded construction, which provide a mechanical attachment between rim 26 and body 21 at proximal end 18. Slider 14 partially extends from the hollow housing 11, out of opening 33, through aperture 28 and vestibule 32.

At distal end 20 of hollow housing 11 is a rear opening 34 leading to internal cavity 24. A base 36 engages body 21 at rear opening 34 to close the internal cavity 24 such that the central longitudinal axis of body 22 intersects the centre point of base 36. Base 36 is not necessary where a two part construction of hollow housing 11, divided lengthwise, is optionally adopted.

Base 36 may be formed as a separate element from body 21. Base 36 may be affixed to body 21 at the distal end 20 by an appropriate adhesive or an inter engaging structure which provides a mechanical attachment therebetween, such as frictional fit, snap fit construction, or threaded engagement or otherwise. Base 36 includes a plate 38. Preferably plate 38 has a border corresponding to body 21. For a snap-fit configuration for an inter-engaging structure between base 36 and body 21, clasps 40 are mounted to one side of plate 38. Clasps 40 have mating surfaces 42 for coupling to corresponding recesses on interior wall 22 of body 21. Clasps 40 are positioned adjacent the border of plate 38 at either sides of the central point of base 36. Body 21 may optionally be provided with guides, on interior 1 wall 22, leading to recesses. When base 36 is engaged to body 21, clasps 40 extend along interior wall 22 with mating surfaces 42 snap fitting into recesses. Clasps 40 are preferably composed of resilient material, it is to be understood that arrangement of the foregoing components of the inter-engaging structure between base 36 and body 21 are merely exemplary and it is contemplated that other inter-engaging structures may be used to fit body 21 with base 36.

The biasing assembly 12 abuts against the base 36 when assembled. Lancet subassembly 13 is engaged to biasing assembly 12 for movement of the lancet subassembly 13 in the hollow housing 11 and for operative interaction between slider 14 and needle holder 16 of the lancet assembly. Biasing assembly 12 is configured to exert a biasing force against needle holder 16 such that needle holder 16 is driven toward the proximal end. The biasing assembly 12 may be a separate element coupled to plate 38 of base 36 or may be integrally formed with plate 38.

Biasing assembly 12 may be a biasing means 46, for example a resilient member such as but not limited to a coil spring, coupled to plate 38 or integrally formed with plate 38. Preferably the biasing means 46 is a metal or plastic spring. Alternatively, biasing assembly may additionally include a coupling member 48 connected to plate 38 of base 36 to couple biasing means 46 to plate 38. Coupling member 48 is positioned at the centre of plate 38 such that when then base 36 engages body 21 at rear opening 38 to close the internal cavity 24, the central longitudinal axis of body 21 intersects coupling member 48. Coupling member 48 supports biasing means 46 in a proper orientation for engagement 1 with lancet subassembly 13. Preferably the coupling member 48 is an alignment boss for accommodating one end of the biasing means 46.

Lancet subassembly 13 may include an engagement member 50 for engagement with the opposite end of the biasing means 46. Preferably, the engagement member 50 is an alignment boss for accommodating the opposite end of the biasing means 46. In a preferred embodiment, biasing means 46 is coupled between coupling member 48 connected to base 36 and engagement member 50 connected to lancet subassembly 13. During initial stages of actuation of lancet device 10, lancet subassembly 13 is pushed axially into hollow housing against biasing assembly 12, causing biasing assembly 12 to store energy, e.g. by compression. Upon release of the compression force, the potential energy stored in the biasing assembly 12 exerts a force against the needle holder 16 of lancet device 12 for biasing the needle holder 16 along the central longitudinal axis 118 of hollow housing 11 towards proximal end 18 to reach the puncture point through vestibule 32. Needle holder 16 reaches the puncture point temporarily. Due to the momentum of the biasing assembly 12 and lancet device, an over extension of the biasing assembly 12 is caused. The biasing assembly 12 then contracts inwards from its over extended condition and the needle holder 16 is retracted into the hollow housing 11. Retraction of the needle holder 16 eliminates the possibility of transmission of blood borne diseases through accidental wounding after use of the lancet.

The lancet subassembly 13 includes the slider 14 and the 1 needle holder 16 which are configured for movement along the central longitudinal axis 118 of hollow housing 11 and subsequent firing of the needle holder 16 for puncturing of the patient's skin or tissue 116.

Needle holder 16 has a longitudinal rotational axis and includes a stem 52 which may be formed as a rod. One end of the stem 52 may be connected to the engagement member 50 and both may be formed a single unit. The opposite end of stem 52 is configured to receive a lance 54. A bore 56 is present partially extending through stem 52, from the end receiving the lance 54. The bore 56 is co-axial with the longitudinal axis 118 of the hollow housing. Bore 56 may be shaped in accordance with the lance 54 which is to be used in lancet device 10.

The lance 54 may be captured within the stem 52 of the needle holder 16 by moulding of the needle holder, or part thereof, onto the lance 54. Alternatively it may be located therein with an interference fit or may have a complimentary structure engagement.

Bore 56 stably retains the lance 54 in needle holder 16. When lance 54 is inserted into bore 56, the lance 54 is aligned along the rotational axis of needle holder 16. Preferably, extending from stem 52 parallel with the rotational axis of needle holder 16 is a sleeve 53. Sleeve 53 extends along the opening of bore 56 at the inner periphery of stem 52. Sleeve 53 provides additional support to lancet 54.

Lancet 54 may be a lancet or a blade having a puncture end 1 58. The puncture end 58 is adapted for puncturing the skin of a patient at a puncture point and may define a pointed end or a blade edge and may also include a preferred alignment orientation.

Needle holder 16 is adapted for longitudinal and rotational movement within hollow housing 11 and is sequentially movable from an initial position with the puncture end 58 within the proximal end 18 of hollow housing 11, to an disengagement position where biasing assembly 12 is compressed and needle holder disengages from slider 14, to a puncturing position in which the puncturing end 58 is biased to extend though vestibule 32 beyond opening 33 (to puncture patient's skin or tissue) and finally to a post-puncture position with the puncture end 58 being withdrawn into hollow housing 11.

The needle holder 16 includes arms 60 attached to stem 52. Each arm 60 extending radially and preferably perpendicular away from the longitudinal axis 118 of needle holder 16. Preferably stem 52 and arms 60 are integrally formed. Each arm 60 is spaced at regular intervals around stem 52 to form gaps 62. It is to be understood that the number of arms 60 may be varied without departing from the spirit of the invention so long at least one gap 62 is provided. For example in some embodiments only one arm 60 may be present.

In an assembled lancet device 10, arms 60 extend from the point of attachment to stem 52 to interior wall 22 and are configured to slidingly contact interior wall 22, during longitudinal and rotational movement of 1 needle holder 16, within hollow housing 11. Preferably, surfaces of arms 60 which contact interior wall 22 are formed with a corresponding curvature to that of interior wall 22. Length of arms 60 are preferably equal and are such that when needle holder 16 is positioned in hollow housing 11, stem 52 is centrally located within hollow housing 11 and between interior wall 22 and the rotational axis of needle holder 16 is aligned to the central longitudinal axis of hollow housing 11.

Each arm 60 includes a drivable surface. In one embodiment the drivable surface is an engagement surface 64 through which the needle holder 16 interacts with slider 14. Each engagement surface 64 has an inner edge attached to stem 52 and an outer edge in movable contact with interior wall 22. Each engagement surface 64 generally faces the proximal end 18 of hollow housing 11. The engagement surface 64 lies on a radial line from the longitudinal axis, in other words it is perpendicular to the longitudinal axis 118. The engagement surface is also rotated about this radial line, so that a normal of the engagement surface is inclined at an angle to the longitudinal axis.

The engagement surface 64 is between a 10° to 80° angle of inclination and in the preferred embodiments has a 45° angle of inclination. The degree of inclination 21 may be varied as will be described hereinafter. The engagement surfaces 64 of each 22 arm 60 are inclined in the same direction and have the same degree of inclination. It 23 is to be understood that arms 60 are formed to provide a platform for engagement 24 with slider 14 during unitary movement therewith and are therefore formed to withstand forces applied to the 1 needle holder.

Slider 14 has a longitudinal axis and includes a disc 66 which defines a puncture surface 68 for contacting the patient's skin to be punctured by the lancet 54. Disc 66 includes an abutment surface 70 opposite the puncture surface 68. Centre point of disc 66 is aligned with the longitudinal axis of slider 14. Disc 66 is movable through vestibule 32 of hollow housing 11. Disc 66 may have a bevelled outer edge which reduces frictional contact between outer edge of disc 66 and wall of collar 30 which encloses vestibule 32. Towards the centre of disc 66 is an inner edge which defines a puncture hole 72. Hole 72 extends through disc 66 in the direction of the longitudinal axis of slider 14. When lancet device 10 is placed against the patient's skin, puncture surface 68 of disc 66 contacts the patient's skin. As lancet device 10 is actuated, part of the patients skin distends into puncture hole 72. After lancet device 10 is actuated, puncture end 58 of lance 54 is fired through puncture hole 72 to puncture the patient's skin.

Longitudinal movement of slider 14 may be limited and rotational movement is preferably restricted as will now be described. Vestibule 32 may include grooves 74 at opposed sides. Each groove 74 being parallel to the central longitudinal axis of hollow housing 11 and extends from the opening 33 of vestibule 32 towards aperture 28. Grooves 74 are separated from the aperture 28 by lips 76. Lips 76 may also be positioned at opening 33 of the vestibule 32. Clip arms 78 may be attached to disc 66 at abutment surface 70. When slider 14 is positioned in hollow housing 11, in an assembled device, disc 66 is slidably enclosed by vestibule 32 with clip arms 78 correspondingly located in and slidably associated with respective 1 grooves 74. Range of longitudinal movement of disc 66, and therefore slider 14, is limited by movement of clip arms 78 along grooves 78, and by lips 76. Disc 66 is restricted from any rotational movement by inter-engagement of clip arms 78 with walls of grooves 74.

Extending from abutment surface 70 are driving portions such as radial props 80. Preferably disc 66 and props 80 are integrally formed. Each prop 80 includes a leg 82 extending parallel to the longitudinal axis of slider 14. At the end of each leg 82 is a radially outward flange 84 extending generally perpendicularly from leg 82 away from the longitudinal axis of slider 14. Length of flange 84 may be equivalent to the breadth of rim 26 between interior wall 22 and edge of aperture 28. A foot 86 extends from each flange 84 generally parallel to leg 82. Outer surface of foot 86 is configured to contact and slide along interior wall 22 during longitudinal movement of slider 14 within hollow housing 11. Preferably, outer surface of each foot 86 which contacts interior wall 22 is formed with a corresponding curvature to that of interior wall 22. The driving portion therefore consists of props 80, legs 82, flanges 84, and feet 86.

At the end of each foot 86 is an inclined driving surface as contact surface 90. In the preferred embodiment the inclination of contact surfaces 90 corresponds and is complimentary to the inclination of engagement surfaces 64 of arms 60.

Figure 11A:
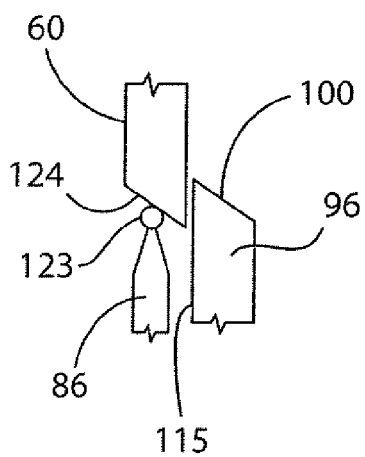
FIG. 11(a)-11(b) show a variation of the interaction of FIG. 10 of the driving surface of the slider and the drivable surface of the needle holder, rather than complimentary planar surfaces, there is shown in FIG. 11a a planar drivable surface of the needle holder that slides on a drivable surface as a following 1 surface (e.g. a smooth round surface) of the slider, whereas in FIG. 11b it is reversed to have the driving surface as the planar driving surface and the drivable surface is a following surface.

In other forms of the invention the driving surface and drivable surface need only be able to slide relative to each other. Many ways to achieve this 1 will be evident to a person skilled in the art. One such way is that shown in FIG. 11. FIG. 11 a shows the arm 60 having an inclined drivable surface as a planar drivable surface 124, which engages a driving surface as a following surface 123, in this case as an extension of the foot 86 of the driving portion. As the driving portion rises up under actuation of the lance 54 the planar drivable surface 124 of the arm 60 will be able to slide or follow over the following surface 123 when clear of the free end 120 of the end wall 100.

Figure 11B:
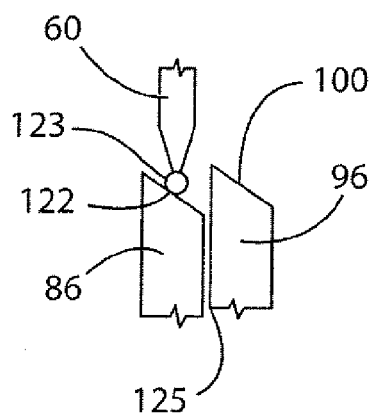
Figure 12:
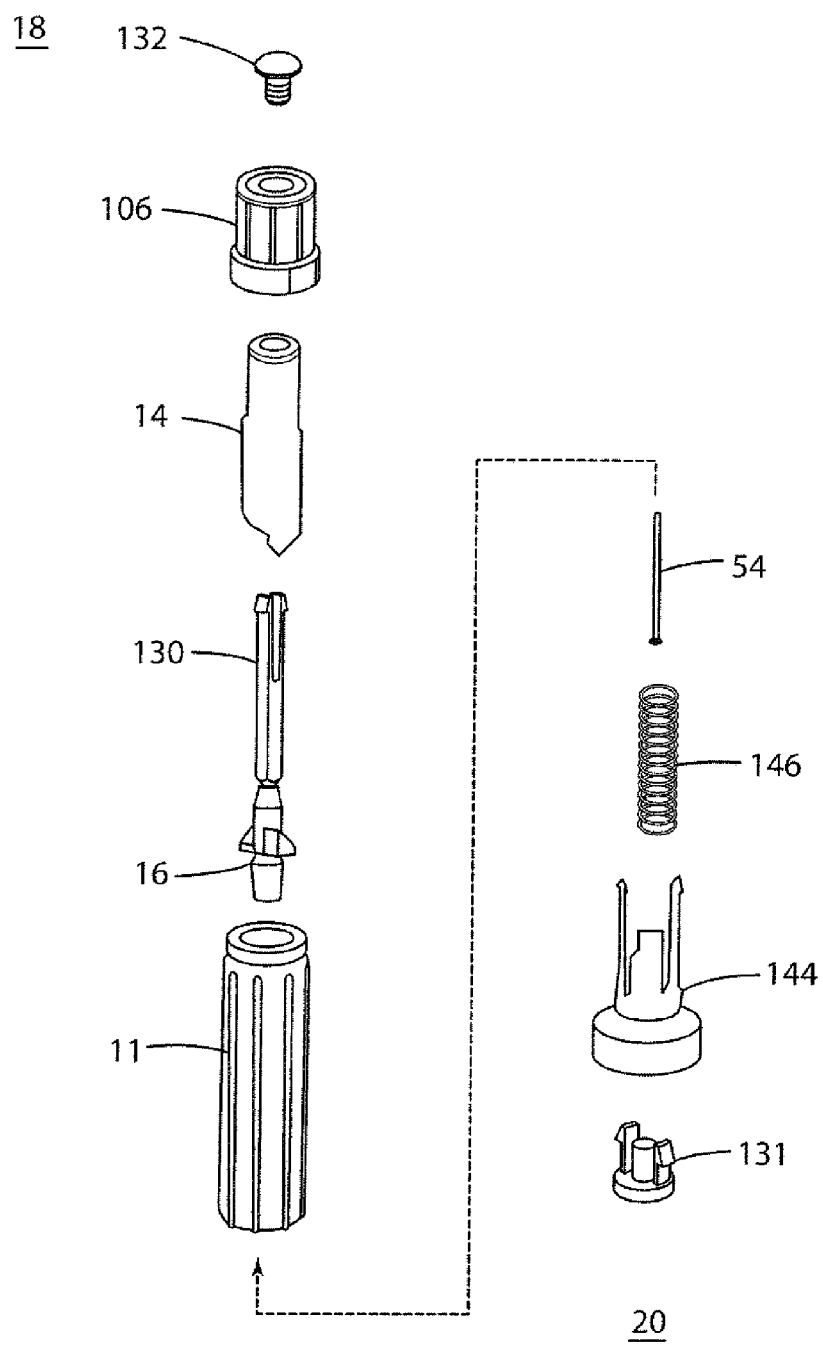
FIG. 12 shows an exploded view of a second embodiment of the present invention.
Figure 13A:
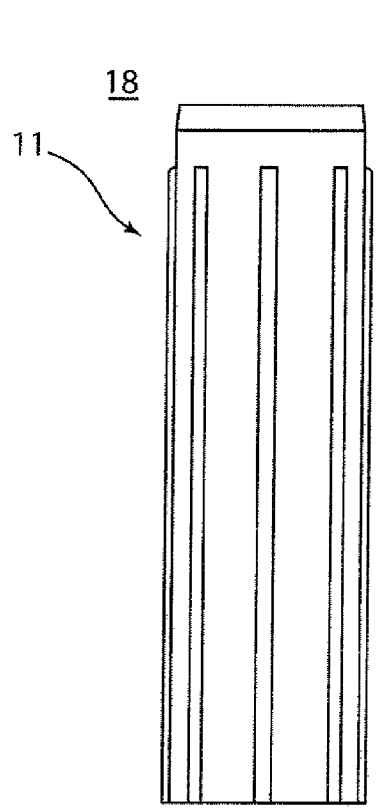
FIG. 13 shows the hollow housing of the second embodiment at (a) front view, (b) vertical section view, (c) bottom view, and (d) isometric view.
Figure 13B:
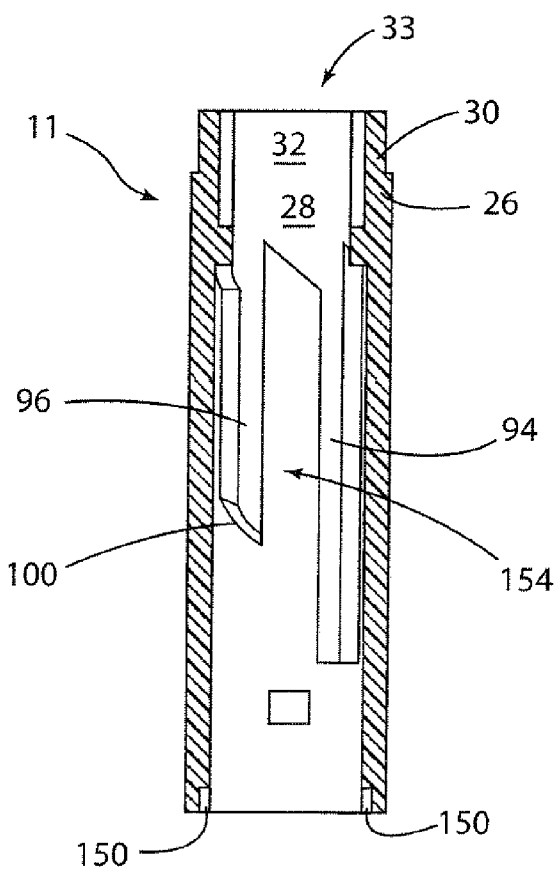
Figure 13C:
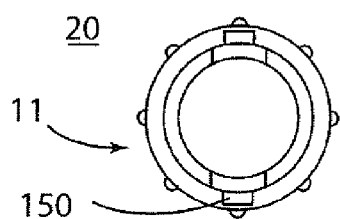
Figure 13D:
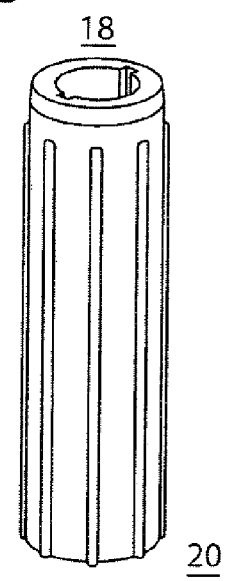
Figure 15A:
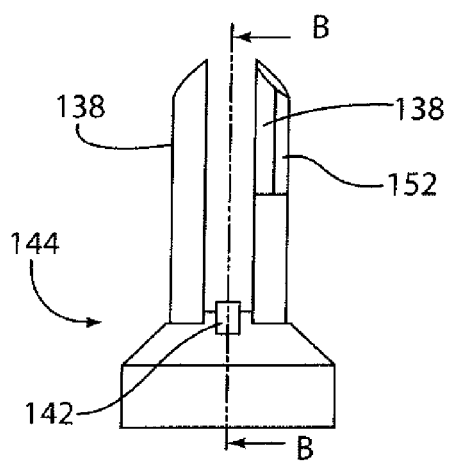
Figure 15B:
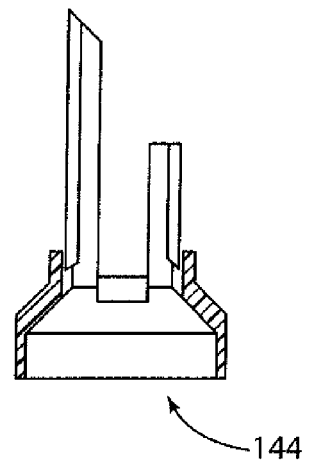
Figure 15C:
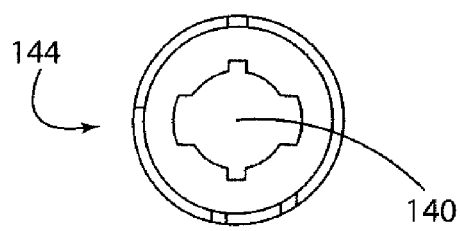
Figure 15D:
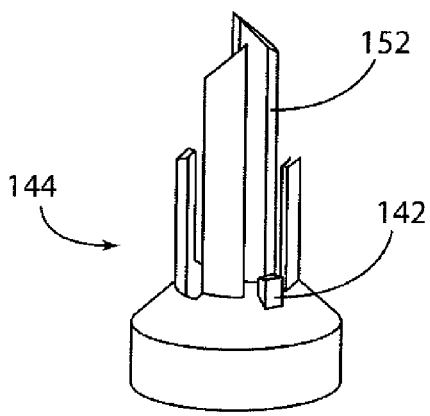
Figure 20A:
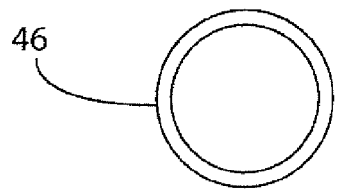
FIG. 20(a)-20(b) show the spring of the second embodiment in (a) plan view and (b) front view.
Figure 20B:
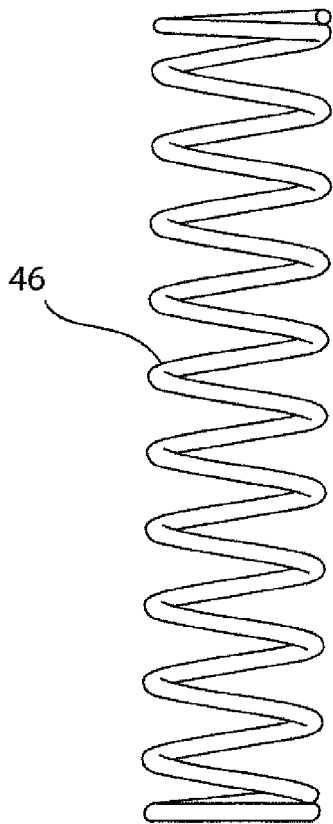

An equivalent opposite structure is shown in FIG. 11b wherein the driving surface is a planar driving surface 122 as part of foot 86 on which the drivable surface as following surface 123 can slide.

In other embodiments the driving surfaces and/or the drivable surfaces and/or the end walls may be curved or otherwise formed provided the drivable surface can slide or pass over the driving surface and the end wall or free end.

The outer edge of arms 60 and outer surface of feet 86 form an even surface. Preferably, flanges 84 are formed parallel to contact surfaces 90 and therefore having the same degree of inclination.

Props 80 are spaced at regular intervals around the outer periphery of disc 66 to form slots 88. Slider 14 and needle holder 16 are moveable towards each other after disengagement by way of arms 60 of needle holder 16 being moveable into slots 88 of slider 14 and props 80 of slider 14 being moveable into 1 gaps 62 of needle holder 16. It is to be understood that the number of props 80 should be the same as the number of arms 60.

When lancet device 10 is assembled, central longitudinal axis of hollow housing 11, axis of slider 14 and rotational axis of needle holder 16 coincide. Prior to actuation of lancet device 10, slider 14 is positioned in hollow housing 11 with engagement surfaces 64 and contact surfaces 90 in frictional engagement. It is to be understood that the degree of inclination may be suitably varied in order to retain engagement surfaces 64 and contact surfaces 90 in frictional engagement till overcome by opposing forces, one acting on slider and the other acting on needle holder 16.

Upon contact of puncture surface 68 with a patient's skin or tissue 116, slider 14 is pushed axially into hollow housing 11 toward the distal end 20. As slider 14 and needle holder 16 are in abutting engagement, both move as a single unit against biasing assembly 12. This results in compression of biasing assembly 12 which results in an increase in the potential energy of biasing assembly 12. As biasing assembly 12 is compressed, the biasing assembly 12 exerts a force against the lancet subassembly 13. Opposing forces thus act on lancet subassembly 13 along the longitudinal axis of hollow housing 11.

As shown in FIGS. 10(a)-10(f), at least one of the driving or drivable surfaces is angled to bias the stem 52 of the needle holder 16 or a surface there of against the guide rail 96 or guide surface 125 thereof during displacement of 1 the needle holder towards the distal end 20. When sufficiently displaced toward the distal end 20 the drivable surface of the needle holder is sent over the free end 120 of the short guide rail 94, due to its being free of rotational constraint of the guide rail 96 or its guide surface 125. The needle holder is then able to rotate about the longitudinal axis 118 and then pass over the free end 120. It is then fired by the biasing means with sufficient momentum toward the proximal end 18 to extend the puncturing end 58 through the proximal end opening 72 with sufficient force to pierce tissue 116 brought into contact therewith. Then the needle holder 52 is retracted by the biasing means sufficient to hold the puncturing end 58 not beyond the proximal end opening 72.

Initially, frictional force between engagement surfaces 64 and contact surfaces 90 is greater than the combined forces from the biasing assembly 12 and from the pushing force from the patient allowing needle holder 16 and slider 14 to move as a single unit. As the lancet device 10 is pressured against the patient lancet subassembly 13 is pushed further into hollow housing 11 thereby increasing the potential energy of biasing assembly and increasing the combined forces on lancet subassembly 13. The combined forces increase until the frictional force between engagement surfaces 64 and contact surfaces 90 is overcome causing engagement surfaces 64 and contact surfaces 90 to slide against each other due to their off axis alignment. Sliding of the surfaces against each other is achieved due to needle holder 16 being able rotate around its rotational axis. But as described herein, slider 14 is unable to under go any rotational movement. Continued increase in the combined forces results in further sliding between engagement 1 surfaces 64 and contact surfaces 90 till the surfaces disengage. Continued relative rotational movement is prevented by arms 60.

In the assembled lancet device 10, contact surfaces 90 of slider 14 have edges which are nearer the distal end 20 and edges which are nearer the distal end 20. Disengagement occurs at the edges nearer the proximal end 18. Each side of feet 86 adjacent the edge nearer the proximal end 18 at which disengagement occurs is hereinafter known as "disengagement side" 92.

Once disengagement occurs, potential energy in the biasing assembly 12 is released to fire the needle holder 16 axially along the central longitudinal axis of hollow housing 11 toward proximal end 18. Needle holder 16 moves towards disc 66 and puncture end 58 of lance 54 slides through puncture hole 72 to reach the puncture point on the patient's skin thereby puncturing the skin. Further movement of needle holder 16 is restricted by stem 52 abutting against abutment surface 70 of disc 66. Biasing assembly 12 then pulls back needle holder 16 into hollow housing 11, to shield puncture end 58 within hollow housing 11.

In one embodiment, interior wall 22 may have a set of guide rails 94, 96 for engaging the feet 86 of slider 14 and for guiding the arms 60 of needle holder 16. Long rails 94 alternate with short rails 96. The number of long rails 94 and number of short rails 96 correspond to the number of props 80 and arms 60. The guide rails extend from rim 26 towards distal end 20, parallel to the central longitudinal axis of housing 11. Between, long rails 94 and short rails 96 are channels 1 or passageways 98. The elongate sides of the guide rails 94, 96 define guide surfaces 125 that guide the elongate portions of the drive portions, i.e. props 80, legs, 82, flanges 84 and feet 86. These guide surfaces also guide the arms 60 until they reach the free end 120 of the end wall 100 of the short rail 96.

In the assembled lancet device 10, feet 86 of slider 14 are held in passageways 98 and guided by guide surfaces 125 to further restrict rotational movement but allow axial movement of slider 14 within hollow housing 11. The number of passageways 98 equals the combined number of feet 86 and arms 60. Hence, in a pre-actuated lancet device 10 there are passageways 98 which remain unoccupied as arms 60 are engaged with feet 86. Preferably, long rails 94 extend beyond the point along hollow housing 11 at which disengagement occurs between needle holder 16 and slider 14. Preferably, short rails 96 extend till the position of contact surfaces 90 on hollow housing 11, when the slider 14 is in a pre-actuated position.

Figure 10A:
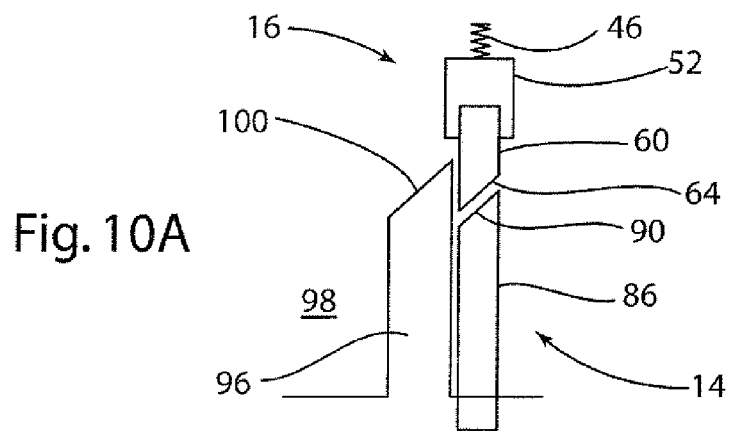
FIGS. 10(a)-10(f) show a zoomed in internal detail of the interface of the needle holder and the slider with the device housing, showing the series of arms of activation, firing and retrieval of the lancet, where.
Figure 10B:
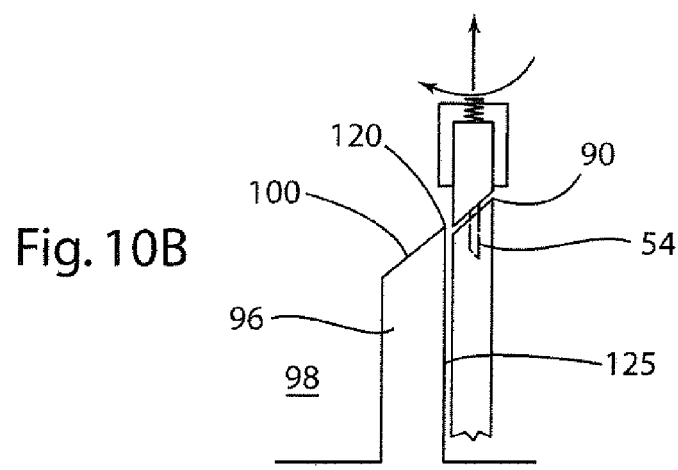
Figure 10C:
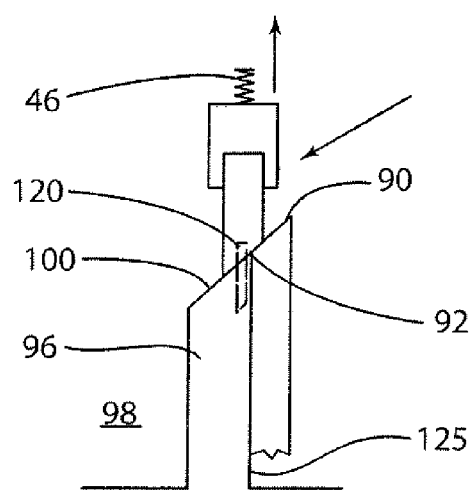
Figure 10D:
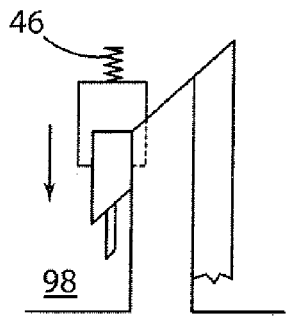
Figure 10E:
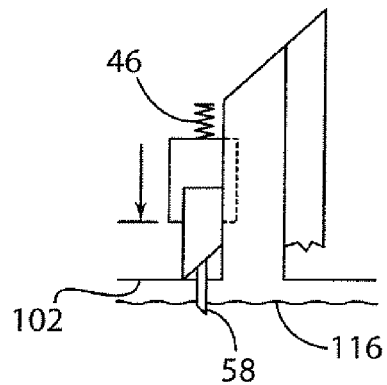
Figure 10F:
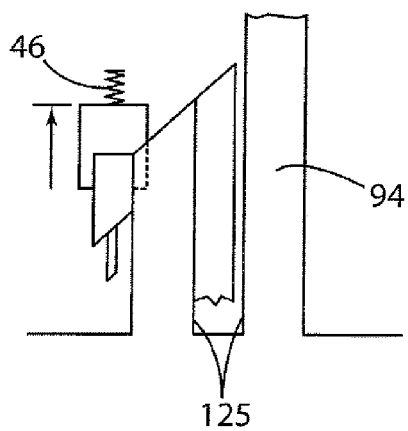

As shown in FIG. 10(a), short rails 96 have end walls 100 which are inclined in the same direction as contact surfaces 90 and correspond to engagement surfaces 64. Short rails 96 are positioned on disengagement side 92 of feet 86. After actuation of lancet device 10, at the moment of disengagement between slider 14 and needle holder 16, contact surfaces 90 are either in line (FIG. 10(b)) with or slightly proud of end walls 100. Hence, arms 60 slide over feet 86 at the disengagement side 92 and slide along end walls 100 by combination of biasing assembly 12 and the angled surfaces. As end walls 100 are correspondingly inclined, engagement 1 surfaces 64 of arms 60 slide along end walls 100 into unoccupied passageways 98 as shown in FIGS. 10(c)-10(d). From there, the lance is free for actuation (free to fire), extending out of the hollow housing and puncturing the skin 116 of a patient. See FIG. 10(e).

Passageways 98 may include ridges 102 extending from rim 26 partway into the passageways 98. Ridges 102 provide abutment surface for flanges 84 of slider 14 and arms 60 of needle holder 16. Longitudinal movement of slider 14 towards proximal end 18 is restricted by abutment of flange 84 and ridge 102. After actuation movement of needle holder 16 towards proximal end 18 is restricted by abutment of arm 60 and ridge 102. Preferably, ridges 102 are inclined correspondingly to engagement surfaces 64 of arm 60.

In one embodiment lancet device 10 may include a cover 104 to protectively cover the puncture surface 68 at distal end 18 of slider 14 prior to actuation of the lancet device 10. Cover 104 maintains sterility prior to use prevents accidental firing of lancet device 10 and acts as a tamper evident structure. Cover 104 includes a cap 106 linked to a ring 108 through frangible links 110. Ring 108 encircles cap 106 and is anchored to the outer periphery of rim 26 through hooks 112. Outer periphery of rim 26 has notches 114 which correspond to hooks 110. To remove cap 106, the patient grips the cap 106 and performs a rotary screw or axial pulling motion thereby breaking the links 110 between cap 106 and ring 108. Once links 110 are broken the cap 106 cannot be replaced. Hence, removal of cap 104 provides a visual identification that the device 10 has been used or tampered with. Optionally, the cover 104 may be excluded. In such an embodiment lance 54 1 is formed with a breakable component which encases the puncture end 58.

The respective elements of device 10 are typically formed of moulded plastic material, such as medical grade plastic material. The lance 54 may be constructed of any suitable material adapted for puncturing the skin and is typically surgical grade metal such as stainless steel.

In one embodiment of assembled lancet device 10, lancet subassembly 13 and biasing assembly 12 are contained within the internal cavity 24 of hollow housing 11. The internal cavity 24 is sealed or and closed at the distal end 20 by base 36. Lancet device is positioned such that disc 66 of slider 14 partially extends at proximal end 18 from hollow housing 11, through opening 33, thereby exposing puncture surface 68. A cover 104 is provided at proximal end 18 over puncture surface 68. Biasing assembly 12 is coupled between the base 36 and lancet subassembly 13. Biasing assembly 12 is compressed by a small degree for imparting a force on lancet subassembly 13 to hold the lancet subassembly 13 in place through abutment of flanges 84 of slider 14 against ridges 102 on interior wail 22 of hollow housing 11. Force imparted by biasing assembly 12 is of sufficient value to maintain, in a pre-actuated lancet device 10, exposure of puncture surface 68 beyond opening 33 of vestibule 32 and to maintain slider 14 and needle holder 16 in engagement. Short rails 96 keep needle holder 16 from rotating and being driven towards proximal end 18 and to the puncture point.

To actuate lancet device 10, a patient or a medical personnel 1 grips body 21 of hollow housing 11 and the cap 106. The cap is first detached by performing a rotary screw or axial pulling motion of the cap 106. The cap 106 is then discarded. Proximal end 18 of hollow housing 11 is then placed onto the patient's skin at a puncture point from which a sample of blood is to be obtained. Specifically the puncture surface 68 of slider 14 contacts the patient's skin. Generally, lancet device 10 should be held perpendicular to the skin.

Still gripping body 21, the user (e.g. the patient or medical professional) begins pushing lancet device 10 against the patient's skin or tissue 116 resulting in lancet subassembly 13 being driven axially into hollow housing 11, along the longitudinal axis, towards proximal end 18. The patient or the medical personnel may place a finger or thumb on base 36 at distal end 20 to impart a greater pushing force to lancet device 10.

As lancet subassembly 13 is driven further into hollow housing 11 against biasing assembly 12, biasing assembly 12 is further compressed. The biasing assembly 12 imparts an opposite force onto the lancet subassembly 13. Rotational movement of slider 14 is limited by abutment of clip arms 78 on disc 66 with lips 76 on the wall enclosing vestibule 32 as well as sliding engagement of props 80 legs 82 and feet 86 against rails-preferably the short rails 96.

Opposed forces from the biasing assembly 12 and slider 14, which receives the pushing force from the patient's skin, act on needle holder 16. Compression of biasing assembly 12 also increases the potential energy stored 1 therein. The combination of the opposed forces increases until the disengagement side 92 of the arm 60 slides away from engagement surface 64 See FIGS. 10(a)-10(c). The surface 64 is then free to slide down end wall 100 as the needle holder rotates resulting in disengagement of needle holder 16 from slider 14. See FIG. 10(d).

Upon disengagement, potential energy in the biasing assembly drives needle holder 16, towards proximal end 18. Needle holder 16 is guided by temporary engagement of arms 60 with end walls 100 of short rails 96 into unoccupied passageways 98. Needle holder 16 continues towards proximal end 18 till arms 60 abut ridges 102 in passageways 98 and stem 52 abuts abutment surface 70. At this point, puncture end 58 of lance 54 temporarily enters puncture hole 72 of slider 14 at proximal end 18 to puncture the patient's skin at the puncture point.

The needle holder 16 then retracts into hollow housing 11 towards distal end 20 by biasing assembly 12 which was in an overextended position due to momentum of lancet subassembly 13 and biasing assembly 12 when puncture end 58 was at the puncture point. Biasing assembly 12 was overextended due to the release of potential energy which carried the biasing assembly 12 to a point of over extension. Retraction of needle holder 16 by biasing assembly 12 pulls puncture end 58 of lance 54 into hollow housing 11 thereby shielding puncture end 58, which may carry blood or other material from the patient, from puncturing skin of another individual. It is to be understood that after actuation of lancet device 10 it is no longer possible to return slider 14 and needle holder 16 to their pre-actuation positions without disassembly of the lancet device 10. This provides an additional 1 safety feature as lancet device 10 can only be used once and should be discarded after use. It should be noted that actuation of lancet device 10 is achieved through sequential arming and release of the needle holder 16 by way of a single continuous motion.

A further embodiment of the present invention will now be described with reference to FIGS. 12-20. Where like integers are present in the second embodiment they refer to the same or similar features as in the first embodiment.

The second embodiment has differences in some of the components of the lance and has some additional components, but otherwise functions in an identical fashion to the first embodiment.

The second embodiment has a cap 106 that attaches indirectly to the hollow housing 11. There is also a cap cover 132 that covers an aperture in the cap 106. A guide body 144 is used for assembly of the slider 14 and the needle holder 16 to the hollow housing 11. There is also a base cap 131 to cover any aperture in the hollow housing 11 distal end. The needle holder 16 in the second embodiment has only two arms 60 as opposed to four in the first embodiment. The arms 60 still have a drivable surface or engagement surface 64 as shown, and the firing functionality of the needle holder 16, slider 14 and housing 11 is identical to that of the first embodiment.

Detailed features of the differences in the second embodiment will now be described.

Toward the proximal end 18 of the needle holder 16 there is a removable guard 130. The removable guard 130 and the needle holder 16 completely cover the lance 54. The removable guard 130 has towards its distal end 18 removable guard clips 134 whose function will shortly be described.

The assembly of the needle holder, lance and removable cover can be accomplished in a number of ways. However in this embodiment the needle holder body and the removable guard 130 are moulded over the lance 54 as shown in FIG. 14. The needle holder 16 and removable guard 130 can be moulded as one or separate pieces over the lance 54. A frangible region 135 as a thin connecting portion between the body of the stem 52 of the needle holder 16 and the removable guard 130 allows breaking of the removable guard 130 from the body of the needle holder 16 for its removal. In other embodiments where the removable guard is moulded separate to the lance body the retention of the removable guard to the lance is by interference fit between the removable guard and the lance. Once the removable guard 130 is removed then the puncturing end 58 of the lance 54 is exposed.

The removable guard functions as a protector for the lance 54 both from a damage and hygiene perspective. The removal of the removable guard 130 at the last possible moment prior to use of the device ensures that the lance is kept hygienic and not damaged. It also protects against damage during assembly and handling of the individual 1 components.

The cap 106 has a base cap aperture 137 through the upper or distal part of its construction. This allows the removable guard clip 134 (as indicated in dotted line in FIG. 18a) to engage with the cap 106, once the needle holder 16 and the slider 14 are assembled in the housing 11. A cap cover 132 engages into the space between the removable guard clip 134 to retain them in an outwards position to engage on the base cap aperture 137; the legs of the cap cover 132 passing into the gap between the removable guard clips 134. The removable guard 130 may engage in other ways to the cap 106. Therefore the removable guard 130 is retained to the cap 106 and the assembly of the cap 106, removable guard 130 and cap cover 132 is removable as a sub-assembly.

There is also present a removable guide body 144 to help with assembly of the lance. The guide body, when engaged with the distal end 20 opening of the hollow housing, allows the assembly of the slider 14 and the needle holder 16 in the correct pre-firing orientation with the hollow housing 11.

FIG. 15(a)-(f) show isometric views of the guide body 144, provided with a guide aperture 140 through its middle. The guide aperture 140 is complimentary to the axial cross-sections of the slider 14 and the needle holder 16. Therefore the slider 14 and needle holder 16 can only be moved through the guide aperture 140 in one rotational orientation.

The guide body 144 also has a locating portion that consists 1 of at least one elongate guide leg 138. In this embodiment there are two such elongate guide legs 138. In addition the locating portion consists of a locating feature 142 that engages in a complimentary feature 150 in the hollow housing 11 when the guide body 144 is inserted into the hollow housing 11. The locating feature 142 will only engage its complimentary feature 150 when the guide body 144 is in the correct rotational orientation about the longitudinal axis.

The elongate guide legs 138 are sufficiently long such that they extend into the hollow housing and abut against the free ends 120 of the short rails 96. If the guide body is in the incorrect orientation, such as the elongate guide legs butting against the free ends of the long rails 94 then the operator/assembly machine can detect this as the guide body will not be is inserted all the way home in the hollow housing 11.

Each elongate guide leg 138 has a guide surface 152 that extends along its length from the guide aperture 140.

The guide aperture 140 and guide surface(s) 152 (and 152a) therefore define a guide for the side surfaces of the drive portions 86 of the slider 14, and the arms 60 of the needle holder 16. The guide body 144 is located in the correct orientation on the distal end of the hollow housing 11, the slider 14 and then the needle holder are passed through the guide aperture (proximal ends first) and pass down into the hollow housing, guided by the guide surface 152 to be located in the channel defined by the short guide rail 96, that is on the pre-firing side 154 of the free 1 end 100 of the short rail 96.

In this embodiment there is a second guide surface 152a extending along the length of a secondary elongate guide leg 138a. This secondary guide surface 152a also extends from the guide aperture 140. The guide surfaces 152 in co-operation with their secondary guide surfaces 152a define a channel from the guide aperture 140 down to the pre-firing side 154 of the short rail 96. In this way the slider 14 and needle holder 16 cannot go anywhere but into the correct location if the guide body is correctly engaged with the hollow housing 11.

In this way the guide body 144 aides in the assembly of the lance and reduces the possibility of incorrect assembly. Once the slider 14 and needle holder 16 are located in the correct pre-firing rotational orientation the guide body 144 can be removed and assembly can continue.

Once assembled in this manner the upper part of the removable guard 130 extends through and presents from the proximal portion proximal end 18 of the slider 14 and hollow housing 11. The cap 106 can then be located over the removable guard clips 134 and secured thereto. Thereafter the cap cover 132 can also be located into place to lock that sub-assembly together. If there is any aperture in the end of the housing 11 distal end of the cover 36 then a base cap 131 engages into the bottom of the base 36. In this way the resulting lance device is better sealed against contaminants and damage.

In using the second embodiment the cap 106 is twisted or pulled and this removes the cap cover 132 and removable guard 130. This exposes the trigger portion of the slider 14 and the lance is then ready to use.

The slider 14 has a longer stroke to fire the lance. To achieve this, the slider has more axial length of trigger portion exposed than the first embodiment. This ensures that it is a positive action that fires the device and not a slight or minor touch to the trigger portion of slider 14.

The hollow housing 11 can also have different external finishing. This is to allow different look and feel to the product. The simplest way of achieving this is to have a changeable cavity side of the moulding that forms the hollow housing 11, for example when the hollow housing is made from injection moulding of a plastic. In this way simple changing of the cavity side with different textures shape or features can allow the finished hollow housing 11 to have different external features. Alternatively, an integral appliqué can be attached to the hollow housing to create different looks to the finished lancet device.

Detailed features of the differences in another highly advantageous embodiment as shown FIG. 21-FIG. 32 will now be described.

Figure 21:
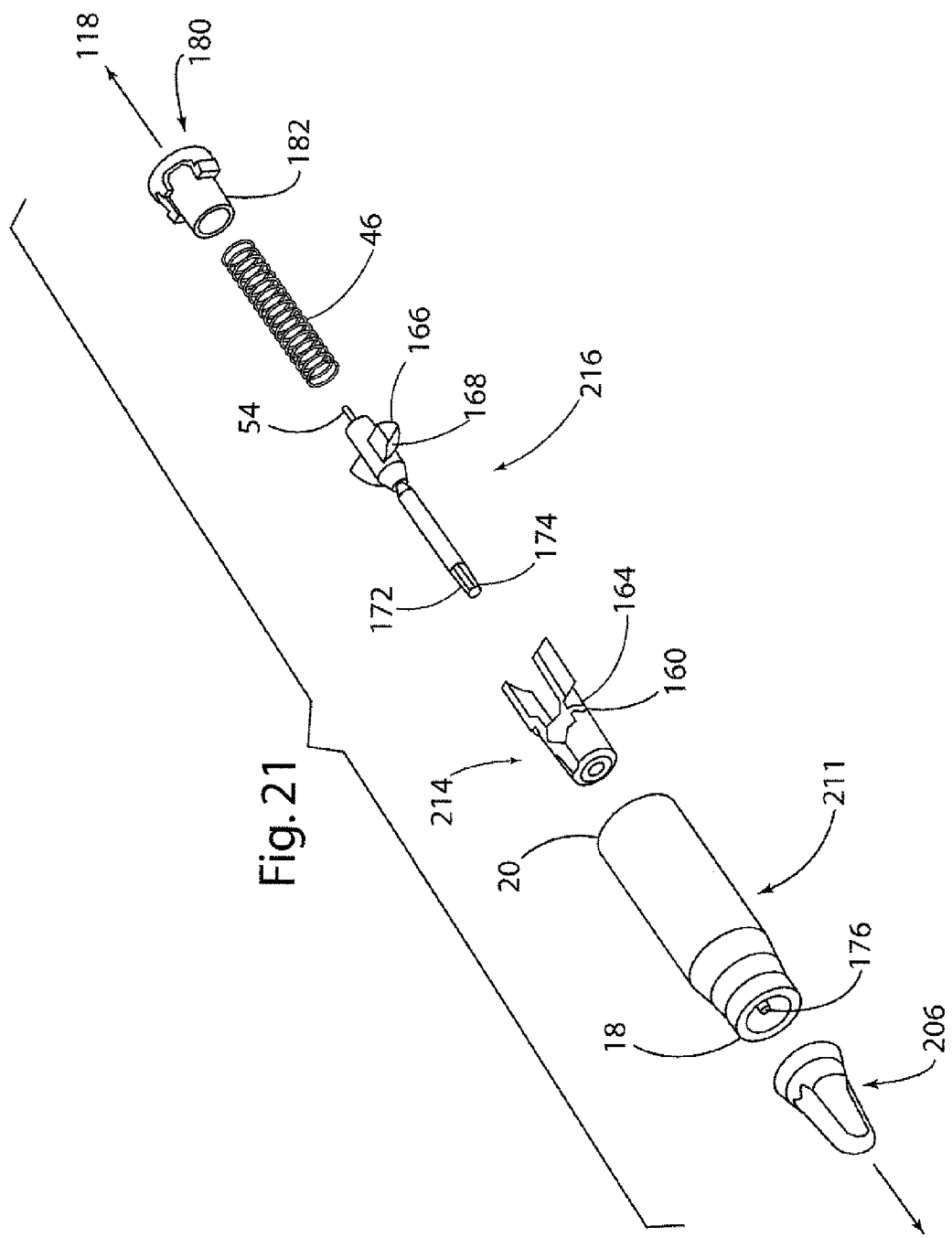
FIG. 21 is an exploded isometric view of another embodiment of the invention showing a slider with an elastic band to help control the holder.

FIG. 21 shows the exploded isometric view of another embodiment, having a 24 cap 206, hollow housing 211, slider 214 with second biasing member 160, needle holder 216, first biasing member 46 and base 180. The hollow housing 1 211 defines a cavity 186, and has a proximal end 18 and a distal end 20.

Figure 24:
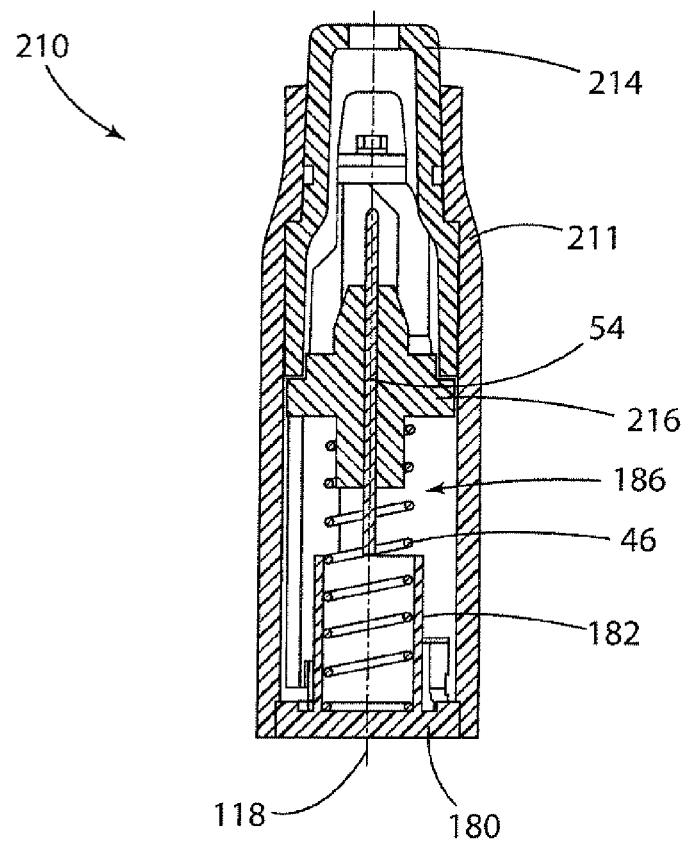
FIG. 24 is a cross section view showing the needle holder in an initial position and the slider in an outward position.
Figure 25:
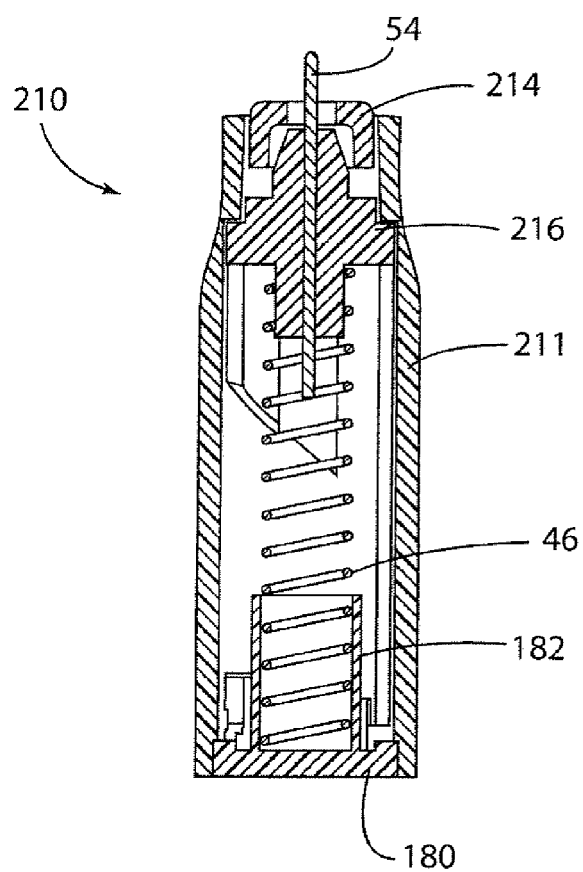
FIG. 25 is a cross section view showing the needle holder in an extended position, extending beyond the proximal end of the hollow housing, and the slider in a pushed position.
Figure 26:
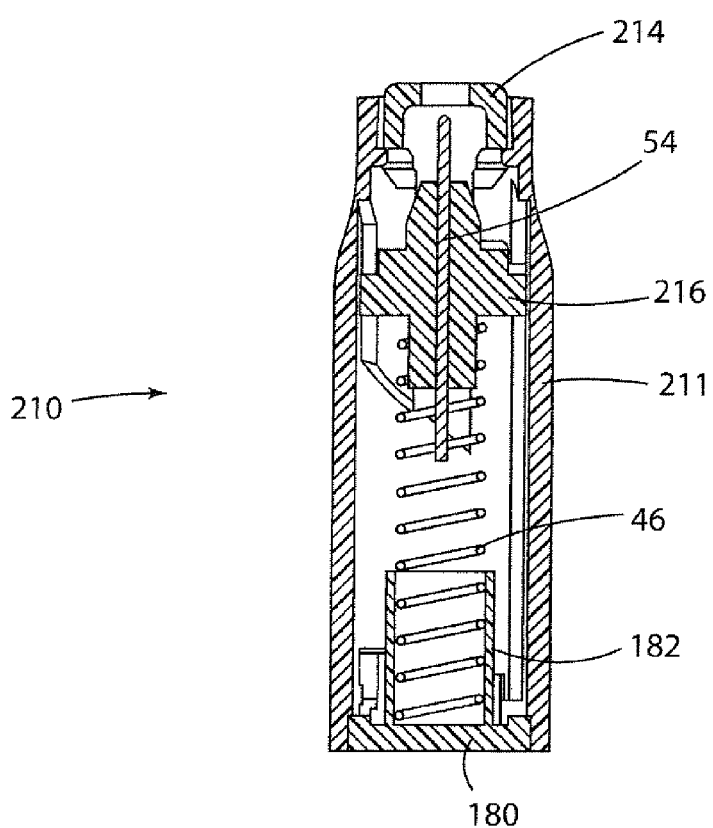
FIG. 26 is a cross section view showing the needle holder 1 in a retracted position, retracted back within the hollow housing, and the slider is in the pushed position.

The slider 214 is slidable at least partially within the cavity 186 of the hollow housing 211 along a longitudinal axis 118 from an outward position to a pushed position. As can be seen in FIG. 24, the slider 214 extends outside of the cavity 186 beyond the proximal end 18 of the hollow housing 211 when in the outward position. In FIG. 25, the sliding of the slider 214 from the outward position to the pushed position urges the needle holder 216 to the extended position.

The needle holder 216 holds a lance 54. In accordance with a highly advantageous feature, the needle holder 216 is rotatable about and translatable along the longitudinal axis 118 when moved from an initial position to an extended position. This helps reduce the likelihood of inadvertent triggering of the lance. When the needle holder 216 is in the initial position, the slider 214 is in the outward position, as shown in FIG. 24. When the needle holder 216 is in the extended position, the lance 54 extends outside of the cavity 186 beyond the proximal end 18 of the hollow housing 211, as in FIG. 25.

The first biasing member 46 is positioned within the hollow housing 211 at the distal end 20. First biasing member 46 exerts a biasing force against the needle holder 216 toward the proximal end 18 when the slider 214 is moved to the pushed position.

Figure 29:
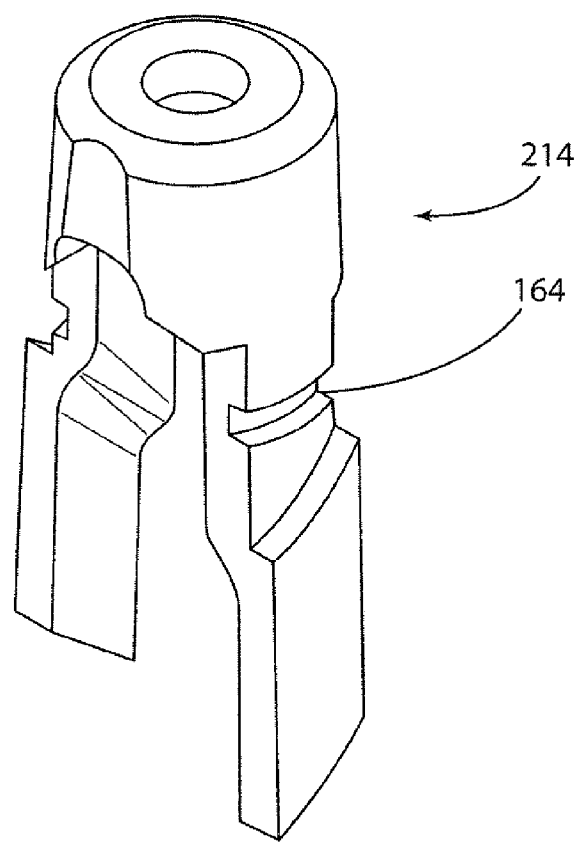
FIG. 29 is an isometric view of the slider with the groove within which the elastic band lies.
Figure 30:
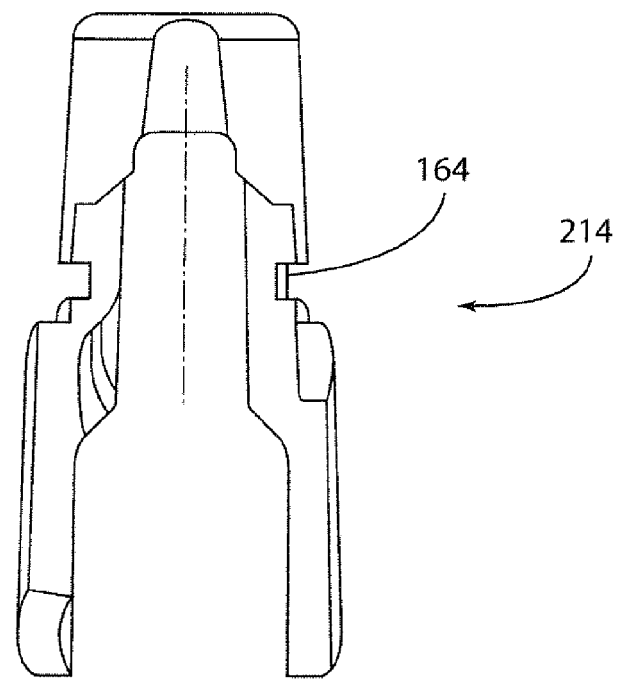
FIG. 30 is a cross section view of the slider with the groove.
Figure 31:
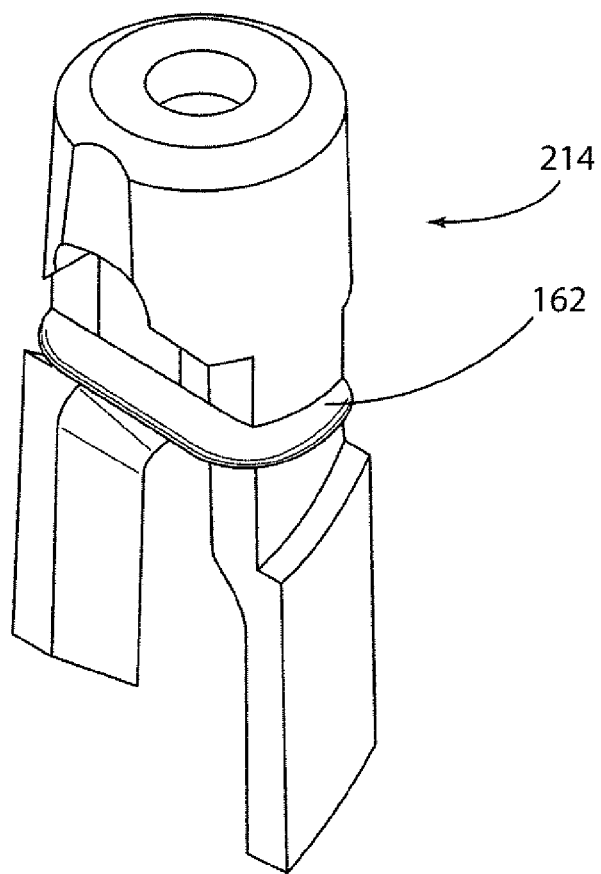
FIG. 31 is an isometric view of the slider with the elastic band within the groove.
Figure 32:
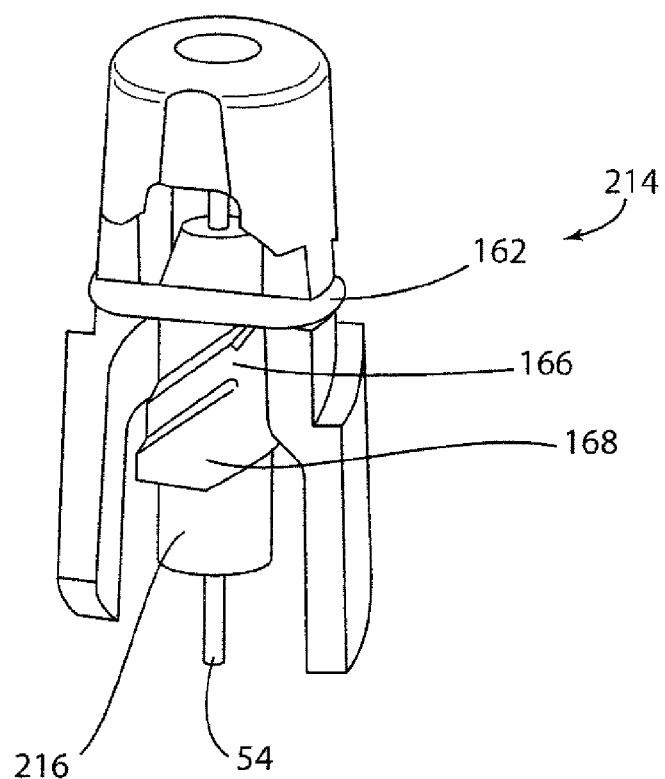
FIG. 32 is an isometric view showing the inner wings of the needle holder engaging the elastic band on the slider.

FIG. 21 shows a second biasing member 160. The second 1 biasing member 160 can be an elastic band 162 or other biasing member, best shown in FIGS. 31-32. The elastic band 162 starts out at rest and is extended or stretched by the needle holder 216 when the needle holder is in the extended position and acts to bias the needle holder back to the retracted position, and thereby return the elastic band to the at rest position. As seen in FIGS. 29-31, the slider 214 has at least one groove 164 on the exterior in which the elastic band 162 is positioned.

Figure 27:
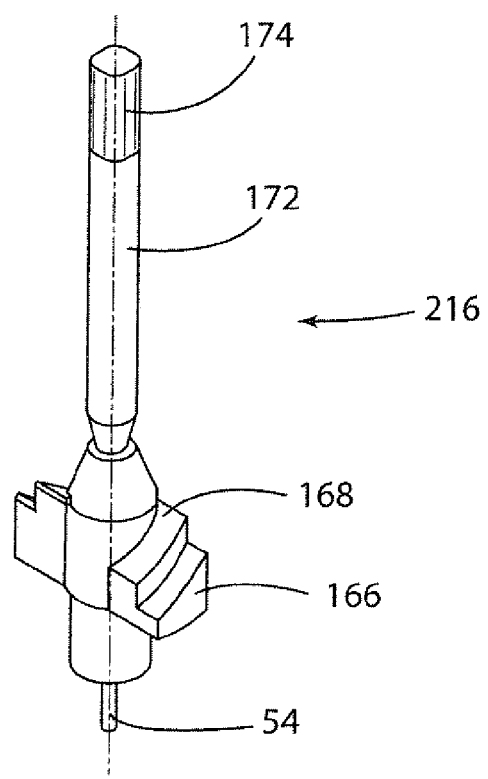
FIG. 27 is an isolated isometric view of the needle holder, showing a pair of inner wings and a pair of outer wings, and the surfaces on the needle guard which are adapted to engage the cap at the cap interior.

The needle holder 216 can comprise a pair of outer wings 166 and inner wings 168. As seen in FIG. 27, the outer wings 166 of the needle holder 216 are closer to the inner wall of the hollow housing 211 than the inner wings 168. The outer wings 166 are optionally angled, so that they slidably engage the slider 214.

When the needle holder 216 is in the extended position and the lance 54 extends outside of the cavity (and optionally has penetrated into the skin 116 of the patient) the needle holder 216 will retract back into the hollow housing 211 due to the biasing force of the biasing assembly 12. In some instances it is desirable to provide additional biasing force to retract the lance 54 back into the hollow housing 211.

The elastic band 162 advantageously helps to bias the needle holder 216 back into the hollow housing 211. When the needle holder 216 is in the extended position, the inner wing 168 of the needle holder 216 is pushed against the elastic band 162. The over-extension of the elastic band 162 causes a build-up in potential energy, which urges the needle holder 216 to move from the extended position to the retracted position. In the retracted position, the lance 54 is retracted 1 back into the hollow housing 211. This can be seen in FIG. 26.

Figure 22:
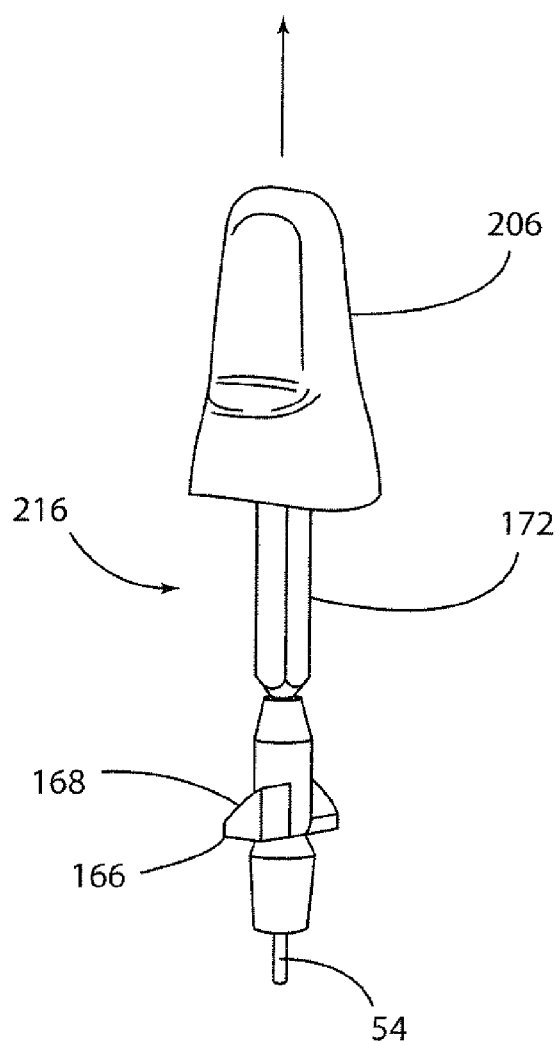
FIG. 22 is a side view of the needle holder of FIG. 21 with the cap attached to a needle guard.
Figure 23:
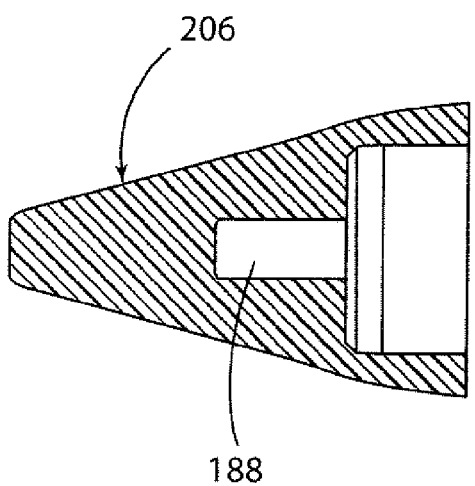
FIG. 23 is a cross section view taken along line A-A of FIG. 22 showing the removable guard of the needle holder in phantom within the cap.

The needle holder 216 further comprises a needle guard 172. The lance 54 is positioned within the needle guard 172. The cap 206 defines an interior 188 (see FIG. 23). FIG. 27 shows the surfaces 174 of the needle guard 172, which are adapted to be received by the interior 188. The surfaces 174 of the needle guard 172 engage the cap 206 at the interior 188. Removal of the needle guard 172 may be readily accomplished by twisting the cap. FIGS. 22 and 23 show how the cap 206 is attached to the needle holder 16. The shape of the cross section of the cap 206 and the needle guard 172 as shown is effective. Other shapes will be readily apparent to those skilled in the art given the benefit of this disclosure.

The cap 206 may be attached to the needle holder 216 by several different ways, e.g. by welding the cap 206 to the needle holder 216, by using adhesive or by using a clip on the needle holder 216 that can clip into an aperture of the cap 206.

Figure 28:
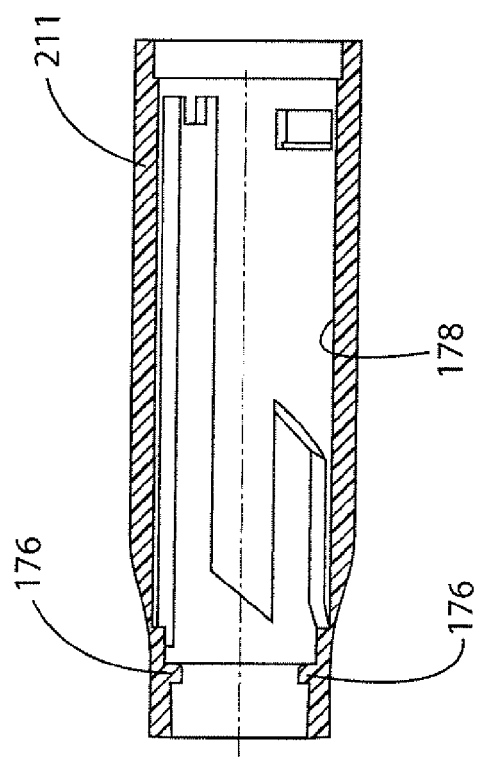
FIG. 28 is a cross section view of the hollow housing, showing at least one stopper element on an interior wall of the hollow housing.

FIG. 28 shows stopper elements 176 in the interior wall 178 of the hollow housing 211. Each stopper element 176 can be formed as a unitary extension on the interior wall 178. As a result of the stopper element 176, movement of the slider 214 towards the distal end 20 is restricted, further reducing the occurrences of the lance 54 protruding out of the slider 214 and hence, out of the hollow housing 211.

A base 180 at the distal end 20 of the lancet device 210 provides closure to the lancet device 210. The spring 46 is positioned between the 1 base 180 and the needle holder 216. The spring 46 is attached to the base 180 at a spring holder 182.

From the foregoing disclosure and detailed description of certain embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A lancet device comprising, in combination:
   a hollow housing defining a cavity and having a proximal end and a distal end;
   a slider slidable at least partially within the cavity of the hollow housing along a longitudinal axis from an outward position to a pushed position, wherein the slider extends outside of the cavity beyond the proximal end of the hollow housing when in the outward position;
   a needle holder holding a needle, wherein the needle holder is adapted to be rotatable about and translatable along the longitudinal axis when moved from an initial position to an extended position, wherein the slider is in the outward position when the needle holder is in the initial position, and the needle extends outside of the cavity beyond the proximal end of the hollow housing when the needle holder is in the extended position;
   a first biasing member positioned within the hollow housing at the distal end, the first biasing member exerting a biasing force against the needle holder toward the proximal end when the slider is moved to the pushed position;
   a second biasing member positioned within the hollow housing at the proximal end, the second biasing member exerting a biasing force against the needle holder toward the distal end when the needle holder is in the extended position; and
   wherein sliding of the slider from the outward position to the pushed position urges the needle holder to the extended position, and wherein the slider has at least one external surface groove and the second biasing member is positioned in the groove.

2. The lancet device of claim 1, wherein the second biasing member is an elastic band attached to the slider.

3. The lancet device of claim 2, wherein the plane within which the groove sits, is orthogonal to the direction of travel of the slider.

4. The lancet device of claim 1, wherein the needle holder comprises a pair of opposed, spaced apart, radially projecting wings, comprising a pair of outer wings and a pair of inner wings, each pair of outer wings being stepped with respect to each pair of inner wings with the outer wings being closer to an inner wall of the hollow housing than the inner wings and wherein the inner wings engage the second biasing member when the needle holder is in the extended position exerting a biasing force to bias the needle holder from the extended position to a retracted position wherein the needle is retracted back into the cavity.

5. The lancet device of claim 4, wherein the outer wings slidably engage the slider.

6. The lancet device of claim 4, wherein the profile of the inner wings are each such that they define an apex which first engages the second biasing member when the needle holder is in the extended position.

7. The lancet device of claim 4, wherein the distance separating respective upper faces of an outer and inner wing of one of the radially projecting wings is the same throughout the entire length of the respective upper surfaces.

* * * * *